(12) United States Patent
Holtzman et al.

US006416974B1

(10) Patent No.: US 6,416,974 B1
(45) Date of Patent: Jul. 9, 2002

(54) TANGO 71 NUCLEIC ACIDS

(75) Inventors: Douglas A. Holtzman, Jamaica Plain; Andrew D. J. Goodearl, Natick, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/130,491

(22) Filed: Aug. 6, 1998

Related U.S. Application Data

(60) Provisional application No. 60/058,108, filed on Sep. 5, 1997, and provisional application No. 60/054,966, filed on Aug. 6, 1997.

(51) Int. Cl.$^7$ .............................. C12P 21/06; C12N 9/00; C12N 1/20; C12N 15/00
(52) U.S. Cl. .................... 435/69.1; 435/183; 435/252.3; 435/320.1; 435/325; 536/23.2; 536/25.1
(58) Field of Search ............................... 536/23.1, 23.2, 536/25.1; 435/183, 227, 69.1, 252.3, 320.1, 325

(56) References Cited

FOREIGN PATENT DOCUMENTS

| EP | 874 050 A2 | 10/1998 |
|----|------------|---------|
| WO | WO 96/01896 | 1/1996 |
| WO | WO 98/56804 | 12/1998 |
| WO | WO 99/37660 | 7/1999 |

OTHER PUBLICATIONS

Briehl et al., "Isolation and Characterization of Transcripts Induced by Androgen Withdrawl and Apoptotic Cell Death" Mol. Endocrinology 5(10):1381–1388, 1991.

Kuno et al., "Molecular Cloning of a Gene Encoding a New Type of Metalloproteinase–disintegrin Family . . . " J. of Biol. Chem. 272(1):556–562, 1997.

Pan et al., "The Receptor for the Cytotoxic Ligand Trail" Science 276:111–113, 1997.

Sirotkin et al., "Identification, Characterization, and Precise Mapping of a Human Gene Encoding a Novel . . . " Genomics 42:245–251, 1997.

Bradham et al., "Connective Tissue Growth Factor: a Cysteine–rich Mitogen Secreted by Human Vascular . . . " J. of Cell. Biol. 114(6):1285–1294, 1991.

Mason et al., "Dorsal midline fate in Drosophila embryos requires twisted gastrulation, a gene encoding . . . " Genes & Developments 8:1489–1501, 1994.

Hillier et al. GenBank Accession No. AA133346, dated May 14, 1997.*

Hudson et al. GenBank Accession No. G06805, dated Oct. 19, 1995.*

Hillier et al. GenBank Accession No. H27128, dated Jul. 12, 1995.*

* cited by examiner

*Primary Examiner*—Rebecca E. Prouty
*Assistant Examiner*—Manjunath N. Rao
(74) *Attorney, Agent, or Firm*—Fish & Richardson, PC

(57) ABSTRACT

The invention relates to Tango-71, Tango-73, Tango-74, Tango-76, and Tango-83 polypeptides, nucleic acid molecules encoding Tango-71, Tango-73, Tango-74, Tango-76, and Tango-83, and uses thereof.

8 Claims, 18 Drawing Sheets

```
gtcgacccac gcgtccgagc ggctccgagc cagggctat tgcaaagcca gggtgcgcta    60
ccggacggag agggagagc cctgagcaga gtgagcaaca tcgcagccaa ggcggaggcc   120
gaagagggc gccaggcacc aatctccgcg ttgcctcagc cccggaggcg ccccagagcg   180
cttcttgtcc cagcagagcc actctgcctg cgcctgcctc tcagtgtctc caactttgcg   240
ctggaagaaa aacttcccgc gcgccggcag aactgcagcg cctcctctta gtgactccgg   300
gagcttcggc tgtagccggc tctgcgcgcc cttccaacga ataatagaaa ttgttaattt   360
taacaatcca gagcaggcca acgaggcttt gctctcccga cccgaactaa agctccctcg   420
ctccgtgcgc tgctacgaac cgtgtctcct ggggctcca atg cag cga gct gtg      474
                                              Met Gln Arg Ala Val
                                               1                 5 ccc gag ggg ttc gga agg cgc aag ctg ggc agc gac atg ggg aac gcg     522
Pro Glu Gly Phe Gly Arg Arg Lys Leu Gly Ser Asp Met Gly Asn Ala
            10                  15                  20 gag cgg gct ccg ggg tct cgg agc ttt ggg ccc gta ccc acg ctg ctg     570
Glu Arg Ala Pro Gly Ser Arg Ser Phe Gly Pro Val Pro Thr Leu Leu
                25                  30                  35 ctg ctc gcc gcg gcg cta ctg gcc gtg tcg gac gca ctc ggg cgc ccc     618
Leu Leu Ala Ala Ala Leu Leu Ala Val Ser Asp Ala Leu Gly Arg Pro
            40                  45                  50 tcc gag gag gac gag gag cta gtg gtg ccg gag ctg gag cgc gcc ccg     666
Ser Glu Glu Asp Glu Glu Leu Val Val Pro Glu Leu Glu Arg Ala Pro
        55                  60                  65 gga cac ggg acc acg cgc ctc cgc ctg cac gcc ttt gac cag cag ctg     714
Gly His Gly Thr Thr Arg Leu Arg Leu His Ala Phe Asp Gln Gln Leu
70                  75                  80                  85
```

FIG. 1A

```
gat ctg gag ctg cgg ccc gac agc agc ttt ttg gcg ccc ggc ttc acg      762
Asp Leu Glu Leu Arg Pro Asp Ser Ser Phe Leu Ala Pro Gly Phe Thr
             90                  95                 100 ctc cag aac gtg ggg cgc aaa tcc ggg tcc gag acg ccg ctt ccg gaa      810
Leu Gln Asn Val Gly Arg Lys Ser Gly Ser Glu Thr Pro Leu Pro Glu
                105                 110                 115 acc gac ctg gcg cac tgc ttc tac tcc ggc acc gtg aat ggc gat ccc      858
Thr Asp Leu Ala His Cys Phe Tyr Ser Gly Thr Val Asn Gly Asp Pro
            120                 125                 130 agc tcg gct gcc gcc ctc agc ctc tgc cag ggc gtg cgc ggc gcc ttc      906
Ser Ser Ala Ala Ala Leu Ser Leu Cys Gln Gly Val Arg Gly Ala Phe
        135                 140                 145 tac ctg ctg ggg gag gcg tat ttc atc cag ccg ctg ccc gcc gcc agc      954
Tyr Leu Leu Gly Glu Ala Tyr Phe Ile Gln Pro Leu Pro Ala Ala Ser
150                 155                 160                 165 gag cgc ctc gcc acc gcc gcc cca ggg gag aag ccg ccg gca cca cta     1002
Glu Arg Leu Ala Thr Ala Ala Pro Gly Glu Lys Pro Pro Ala Pro Leu
                170                 175                 180 cag ttc cac ctc ctg cgg cgg aat cgg cag ggc gac gta ggc ggc acg     1050
Gln Phe His Leu Leu Arg Arg Asn Arg Gln Gly Asp Val Gly Gly Thr
            185                 190                 195 tgc ggg gtc gtg gac gac gag ccc cgg ccg act ggg aaa gcg gag acc     1098
Cys Gly Val Val Asp Asp Glu Pro Arg Pro Thr Gly Lys Ala Glu Thr
        200                 205                 210 gaa gac gag gac gaa ggg act gag ggc gag gac gaa ggg cct cag tgg     1146
Glu Asp Glu Asp Glu Gly Thr Glu Gly Glu Asp Glu Gly Pro Gln Trp
    215                 220                 225 tcg ccg cag gac ccg gca ctg caa ggc gta gga cag ccc aca gga act     1194
Ser Pro Gln Asp Pro Ala Leu Gln Gly Val Gly Gln Pro Thr Gly Thr
230                 235                 240                 245 gga agc ata aga aag aag cga ttt gtg tcc agt cac cgc tat gtg gaa     1242
Gly Ser Ile Arg Lys Lys Arg Phe Val Ser Ser His Arg Tyr Val Glu
                250                 255                 260 acc atg ctt gtg gca gac cag tcg atg gca gaa ttc cac ggc agt ggt     1290
Thr Met Leu Val Ala Asp Gln Ser Met Ala Glu Phe His Gly Ser Gly
            265                 270                 275 cta aag cat tac ctt ctc acg ttg ttt tcg gtg gca gcc aga ttg tac     1338
Leu Lys His Tyr Leu Leu Thr Leu Phe Ser Val Ala Ala Arg Leu Tyr
        280                 285                 290 aaa cac ccc agc att cgt aat tca gtt agc ctg gtg gtg gtg aag atc     1386
Lys His Pro Ser Ile Arg Asn Ser Val Ser Leu Val Val Val Lys Ile
    295                 300                 305 ttg gtc atc cac gat gaa cag aag ggg ccg gaa gtg acc tcc aat gct     1434
Leu Val Ile His Asp Glu Gln Lys Gly Pro Glu Val Thr Ser Asn Ala
310                 315                 320                 325
```

FIG. 1B

```
gcc ctc act ctg cgg aac ttt tgc aac tgg cag aag cag cac aac cca      1482
Ala Leu Thr Leu Arg Asn Phe Cys Asn Trp Gln Lys Gln His Asn Pro
            330                 335                 340 ccc agt gac cgg gat gca gag cac tat gac aca gca att ctt ttc acc      1530
Pro Ser Asp Arg Asp Ala Glu His Tyr Asp Thr Ala Ile Leu Phe Thr
                345                 350                 355 aga cag gac ttg tgt ggg tcc cag aca tgt gat act ctt ggg atg gct      1578
Arg Gln Asp Leu Cys Gly Ser Gln Thr Cys Asp Thr Leu Gly Met Ala
            360                 365                 370 gat gtt gga act gtg tgt gat ccg agc aga agc tgc tcc gtc ata gaa      1626
Asp Val Gly Thr Val Cys Asp Pro Ser Arg Ser Cys Ser Val Ile Glu
375                 380                 385 gat gat ggt tta caa gct gcc ttc acc aca gcc cat gaa tta ggc cac      1674
Asp Asp Gly Leu Gln Ala Ala Phe Thr Thr Ala His Glu Leu Gly His
390                 395                 400                 405 gtg ttt aac atg cca cat gat gat gca aag cag tgt gcc agc ctt aat      1722
Val Phe Asn Met Pro His Asp Asp Ala Lys Gln Cys Ala Ser Leu Asn
                410                 415                 420 ggt gtg aac cag gat tcc cac atg atg gcg tca atg ctt tcc aac ctg      1770
Gly Val Asn Gln Asp Ser His Met Met Ala Ser Met Leu Ser Asn Leu
            425                 430                 435 gac cac agc cag cct tgg tct cct tgc agt gcc tac atg att aca tca      1818
Asp His Ser Gln Pro Trp Ser Pro Cys Ser Ala Tyr Met Ile Thr Ser
            440                 445                 450 ttt ctg gat aat ggt cat cgg gaa tgt ttg atg gac aag cct cag aat      1866
Phe Leu Asp Asn Gly His Arg Glu Cys Leu Met Asp Lys Pro Gln Asn
            455                 460                 465 ccc ata cag ctc cca ggc gat ctc cct ggc acc tcg tac gat gcc aac      1914
Pro Ile Gln Leu Pro Gly Asp Leu Pro Gly Thr Ser Tyr Asp Ala Asn
470                 475                 480                 485 cgg cag tgc cag ttt aca ttt ggg gag gac tcc aaa cac tgc ccc gat      1962
Arg Gln Cys Gln Phe Thr Phe Gly Glu Asp Ser Lys His Cys Pro Asp
                490                 495                 500 gca gcc agc aca tgt agc acc ttg tgg tgt acc ggc acc tct ggt ggg      2010
Ala Ala Ser Thr Cys Ser Thr Leu Trp Cys Thr Gly Thr Ser Gly Gly
            505                 510                 515 gtg ctg gtg tgt caa acc aaa cac ttc ccg tgg gcg gat ggc acc agc      2058
Val Leu Val Cys Gln Thr Lys His Phe Pro Trp Ala Asp Gly Thr Ser
            520                 525                 530 tgt gga gaa ggg aaa tgg tgt atc aac ggc aag tgt gtg aac aaa acc      2106
Cys Gly Glu Gly Lys Trp Cys Ile Asn Gly Lys Cys Val Asn Lys Thr
            535                 540                 545 gac aga aag cat ttt gat acg cct ttt cat gga agc tgg gga atg tgg      2154
Asp Arg Lys His Phe Asp Thr Pro Phe His Gly Ser Trp Gly Met Trp
550                 555                 560                 565
```

FIG. 1C

```
ggg cct tgg gga gac tgt tcg aga acg tgc ggt gga gga gtc cag tac    2202
Gly Pro Trp Gly Asp Cys Ser Arg Thr Cys Gly Gly Gly Val Gln Tyr
                570             575             580 acg atg agg gaa tgt gac aac cca gtc cca aag aat gga ggg aag tac    2250
Thr Met Arg Glu Cys Asp Asn Pro Val Pro Lys Asn Gly Gly Lys Tyr
                585             590             595 tgt gaa ggc aaa cga gtg cgc tac aga tcc tgt aac ctt gag gac tgt    2298
Cys Glu Gly Lys Arg Val Arg Tyr Arg Ser Cys Asn Leu Glu Asp Cys
                600             605             610 cca gac aat aat gga aaa acc ttt aga gag gaa caa tgt gaa gca cac    2346
Pro Asp Asn Asn Gly Lys Thr Phe Arg Glu Glu Gln Cys Glu Ala His
                615             620             625 aac gag ttt tca aaa gct tcc ttt ggg agt ggg cct gcg gtg gaa tgg    2394
Asn Glu Phe Ser Lys Ala Ser Phe Gly Ser Gly Pro Ala Val Glu Trp
630             635             640             645 att ccc aag tac gct ggc gtc tca cca aag gac agg tgc aag ctc atc    2442
Ile Pro Lys Tyr Ala Gly Val Ser Pro Lys Asp Arg Cys Lys Leu Ile
                650             655             660 tgc caa gcc aaa ggc att ggc tac ttc ttc gtt ttg cag ccc aag gtt    2490
Cys Gln Ala Lys Gly Ile Gly Tyr Phe Phe Val Leu Gln Pro Lys Val
                665             670             675 gta gat ggt act cca tgt agc cca gat tcc acc tct gtc tgt gtg caa    2538
Val Asp Gly Thr Pro Cys Ser Pro Asp Ser Thr Ser Val Cys Val Gln
                680             685             690 gga cag tgt gta aaa gct ggt tgt gat cgc atc ata gac tcc aaa aag    2586
Gly Gln Cys Val Lys Ala Gly Cys Asp Arg Ile Ile Asp Ser Lys Lys
                695             700             705 aag ttt gat aaa tgt ggt gtt tgc ggg gga aat gga tct act tgt aaa    2634
Lys Phe Asp Lys Cys Gly Val Cys Gly Gly Asn Gly Ser Thr Cys Lys
710             715             720             725 aaa ata tca gga tca gtt act agt cca aaa cct gga tat cat gat atc    2682
Lys Ile Ser Gly Ser Val Thr Ser Ala Lys Pro Gly Tyr His Asp Ile
                730             735             740 atc aca att cca act gga gcc acc aac atc gaa gtg aaa cag cgg aac    2730
Ile Thr Ile Pro Thr Gly Ala Thr Asn Ile Glu Val Lys Gln Arg Asn
                745             750             755 cag agg gga tcc agg aac aat ggc agc ttt ctt gcc atc aaa gct gct    2778
Gln Arg Gly Ser Arg Asn Asn Gly Ser Phe Leu Ala Ile Lys Ala Ala
                760             765             770 gat ggc aca tat att ctt aat ggt gac tac act ttg tcc acc tta gag    2826
Asp Gly Thr Tyr Ile Leu Asn Gly Asp Tyr Thr Leu Ser Thr Leu Glu
                775             780             785 caa gac att atg tac aaa ggt gtt gtc ttg agg tac agc ggc tcc tct    2874
Gln Asp Ile Met Tyr Lys Gly Val Val Leu Arg Tyr Ser Gly Ser Ser
790             795             800             805
```

FIG. 1D

| | | | | | | | | | | | | | | |
|---|---|---|---|---|---|---|---|---|---|---|---|---|---|---|
| gcg | gca | ttg | gaa | aga | att | cgc | agc | ttt | agc | cct | ctc | aaa | gag | ccc | ttg | 2922 |
| Ala | Ala | Leu | Glu | Arg<br>810 | Ile | Arg | Ser | Phe | Ser<br>815 | Pro | Leu | Lys | Glu | Pro<br>820 | Leu |

| acc | atc | cag | gtt | ctt | act | ctg | ggc | aat | gcc | ctt | cga | cct | aaa | att | aaa | 2970 |
| Thr | Ile | Gln | Val | Leu<br>825 | Thr | Val | Gly | Asn | Ala<br>830 | Leu | Arg | Pro | Lys<br>835 | Ile | Lys |

| tac | acc | tac | ttc | gta | aag | aag | aag | gaa | tct | ttc | aat | gct | atc | ccc | 3018 |
| Tyr | Thr | Tyr<br>840 | Phe | Val | Lys | Lys<br>845 | Lys | Glu | Ser | Phe | Asn<br>850 | Ala | Ile | Pro |

| act | ttt | tca | gca | tgg | gtc | att | gaa | gag | tgg | ggc | gaa | tgt | tct | aag | tca | 3066 |
| Thr | Phe | Ser<br>855 | Ala | Trp | Val | Ile | Glu<br>860 | Glu | Trp | Gly | Glu<br>865 | Cys | Ser | Lys | Ser |

| tgt | gaa | ttg | ggt | tgg | cag | aga | aga | ctg | gta | gaa | tgc | cga | gac | att | aat | 3114 |
| Cys<br>870 | Glu | Leu | Gly | Trp | Gln<br>875 | Arg | Arg | Leu | Val | Glu<br>880 | Cys | Arg | Asp | Ile | Asn<br>885 |

| gga | cag | cct | gct | tcc | gag | tgt | gca | aag | gaa | gtg | aag | cca | gcc | agc | acc | 3162 |
| Gly | Gln | Pro | Ala | Ser<br>890 | Glu | Cys | Ala | Lys | Glu<br>895 | Val | Lys | Pro | Ala | Ser<br>900 | Thr |

| aga | cct | tgt | gca | gac | cat | ccc | tgc | ccc | cag | tgg | cag | ctg | ggg | gag | tgg | 3210 |
| Arg | Pro | Cys | Ala | Asp<br>905 | His | Pro | Cys | Pro | Gln<br>910 | Trp | Gln | Leu | Gly | Glu<br>915 | Trp |

| tca | tca | tgt | tct | aag | acc | tgt | ggg | aag | ggt | tac | aaa | aaa | aga | agc | ttg | 3258 |
| Ser | Ser | Cys<br>920 | Ser | Lys | Thr | Cys | Gly<br>925 | Lys | Gly | Tyr | Lys | Lys<br>930 | Arg | Ser | Leu |

| aag | tgt | ctg | tcc | cat | gat | gga | ggg | gtg | tta | tct | cat | gag | agc | tgt | gat | 3306 |
| Lys | Cys<br>935 | Leu | Ser | His | Asp | Gly<br>940 | Gly | Val | Leu | Ser | His<br>945 | Glu | Ser | Cys | Asp |

| cct | tta | aag | aaa | cct | aaa | cat | ttc | ata | gac | ttt | tgc | aca | atg | gca | gaa | 3354 |
| Pro | Leu<br>950 | Lys | Lys | Pro | Lys<br>955 | His | Phe | Ile | Asp | Phe<br>960 | Cys | Thr | Met | Ala | Glu<br>965 |

| tgc | agt | taagtggttt | aagtggtgtt | agctttgagg | gcaaggcaaa | gtgaggaagg | 3410 |
| Cys | Ser | | | | | |

```
gctggtgcag ggaaagcaag aaggctggag ggatccagcg tatcttgcca gtaaccagtg    3470
aggtgtatca gtaaggtggg attatggggg tagatagaaa aggagttgaa tcatcagagt    3530
aaactgccag ttgcaaattt gataggatag ttagtgagga ttattaacct ctgagcagtg    3590
atatagcata ataaagcccc gggcattatt attattattt cttttgttac atctattaca    3650
agtttagaaa aaacaaagca attgtcaaaa aaagttagaa ctattacaac ccctgttttcc    3710
tggtacttat caaatactta gtatcatggg ggttgggaaa tgaaaagtag gagaaagtg     3770
agattttact aagacctgtt ttactttacc tcactaacaa tggggggaga aggagtaca     3830
aataggatct tgaccagca ctgttatgg ctgctgtggt tcagagaat gttatacat      3890
tatttctacc gagaattaaa acttcagatt gttcaacatg agagaaggc tcagcaacgt    3950
gaataacgc aaatggcttc ctctttcctt ttttggacca tctcagtctt tatttgtgta    4010
attcattttg aggaaaaac aactccatgt atttattcaa gtgcattaaa gtctacaatg    4070
gaaaaaaagc agtgaagcat tacatgctgg taaaagctag aggagacaca atgagcttag    4130
tacctccaac ttcctttctt tcctaccatg taaccctgct tcggaatat ggatgtaaag     4190
aagtaacttg tgtctcatga aaatcagtac aatcacacaa ggaggatgaa acgccggaac    4250
aaaaatgagg tgtgtagaac agggtccac aggtttgggg acattgagat cacttgtctt    4310
gtggtgggga ggctgctgag gggtagcagg tccatctcca gcagctggtc caacagtcgt    4370
atcctggtga atgtctgttc agctcttctg tgagaatatg attttttcca tatgtatata    4430
gtaaaatatg ttactataa ttacatgtac tttataagta ttggtttggg tgttccttcc    4490
aagaaggact atagttagta ataaatgcct ataataacat atttattttt atacatttat    4550
ttctaatgaa aaaaactttt aaattatatc gcttttgtgg aagtgcatat aaaatagagt    4610
atttatacaa tatatgttac tagaaataaa agaacacttt tggaaaaaaa aaaaaaaaaa    4670
aaaaaa                                                                 4676
```

FIG. 1E

```
gtcgacccac gcgtccgggg agcaaccgca gcttctagta tccagactcc agcgccgccc    60
cgggcgcgga ccccaacccc gacccagagc ttctccagcg gcggcgcagc gagcagggct   120
ccccgcctta acttcctccg cggggcccag ccaccttcgg gagtccgggt tgcccaccte   180
caaactctcc gccttctgca cctgccaccc ctgagccagc gcgggcgccc gagccagtc    239
atg gcc aac gcg ggg ctg cag ctg ttg ggc ttc att ctc gcc ttc ctg    287
Met Ala Asn Ala Gly Leu Gln Leu Leu Gly Phe Ile Leu Ala Phe Leu
 1           5                   10                  15 gga tgg atc ggc gcc atc gtc agc act gcc ctg ccc cag tgg agg att    335
Gly Trp Ile Gly Ala Ile Val Ser Thr Ala Leu Pro Gln Trp Arg Ile
             20                  25                  30 tac tcc tat gcc ggc gac aac atc gtg acc gcc cag gcc atg tac gag    383
Tyr Ser Tyr Ala Gly Asp Asn Ile Val Thr Ala Gln Ala Met Tyr Glu
                 35                  40                  45 ggg ctg tgg atg tcc tgc gtg tcg cag agc acc ggg cag atc cag tgc    431
Gly Leu Trp Met Ser Cys Val Ser Gln Ser Thr Gly Gln Ile Gln Cys
     50                  55                  60 aaa gtc ttt gac tcc ttg ctg aat ctg agc agc aca ttg caa gca acc    479
Lys Val Phe Asp Ser Leu Leu Asn Leu Ser Ser Thr Leu Gln Ala Thr
 65                  70                  75                  80 cgt gcc ttg atg gtg gtt ggc atc ctc ctg gga gtg ata gca atc ttt    527
Arg Ala Leu Met Val Val Gly Ile Leu Leu Gly Val Ile Ala Ile Phe
                 85                  90                  95 gtg gcc acc gtt ggc atg aag tgt atg aag tgc ttg gaa gac gat gag    575
Val Ala Thr Val Gly Met Lys Cys Met Lys Cys Leu Glu Asp Asp Glu
            100                 105                 110 gtg cag aag atg agg atg gct gtc att ggg ggt gcg ata ttt ctt ctt    623
Val Gln Lys Met Arg Met Ala Val Ile Gly Gly Ala Ile Phe Leu Leu
            115                 120                 125 gca ggt ctg gct att tta gtt gcc aca gca tgg tat ggc aat aga atc    671
Ala Gly Leu Ala Ile Leu Val Ala Thr Ala Trp Tyr Gly Asn Arg Ile
130                 135                 140
```

FIG. 2A

```
gtt caa gaa ttc tat gac cct atg acc cca gtc aat gcc agg tac gaa      719
Val Gln Glu Phe Tyr Asp Pro Met Thr Pro Val Asn Ala Arg Tyr Glu
145                 150                 155                 160 ttt ggt cag gct ctc ttc act ggc tgg gct gct gct tct ctc tgc ctt      767
Phe Gly Gln Ala Leu Phe Thr Gly Trp Ala Ala Ala Ser Leu Cys Leu
                    165                 170                 175 ctg gga ggt gcc cta ctt tgc tgt tcc tgt ccc cga aaa aca acc tct      815
Leu Gly Gly Ala Leu Leu Cys Cys Ser Cys Pro Arg Lys Thr Thr Ser
                180                 185                 190 tac cca aca cca agg ccc tat cca aaa cct gca cct tcc agc ggg aaa      863
Tyr Pro Thr Pro Arg Pro Tyr Pro Lys Pro Ala Pro Ser Ser Gly Lys
            195                 200                 205 gac tac gtg tgacacagag gcaaaaggag aaaatcatgt tgaaacaaac              912
Asp Tyr Val
    210 cgaaaatgga cattgagata ctatcattaa cattaggacc ttagaatttt gggtattgta    972
atctgaagta tggtattaca aaacaaacaa acaaacaaaa aacccatgtg ttaaaatact   1032
cagtgctaaa catggcttaa tcttatttta tcttctttcc tcaatatagg agggaagatt   1092
tttccatttg tattactgct tcccattgag taatcatact caactggggg aagggtgct    1152
ccttaaatat atatagatat gtatatatac atgtttttct attaaaaata gacagtaaaa   1212
tactattctc attatgttga tactagcata cttaaaatat ctctaaaata ggtaaatgta   1272
tttaattcca tattgatgaa gatgtttatt ggtatatttt cttttcgtc tatatataca    1332
tatgtaacag tcaaatatca tttactcttc ttcattagct ttgggtgcct ttgccacaag   1392
acctagccta atttaccaag gatgaattct ttcaattctt catgcgtgcc cttttcatat   1452
acttatttta tttttttacca taatcttata gcacttgcat cgttattaag cccttatttg  1512
ttttgtgttt cattggtctc tatctcctga atctaacaca tttcatagcc tacattttag   1572
tttctaaagc caagaagaat ttattacaaa tcagaacttt ggaggcaaat ctttctgcat   1632
gaccaaagtg ataaattcct gttgaccttc ccacacaatc cctgtactct gacccatagc   1692
actcttgttt gctttgaaaa tatttgtcca attgagtagc tgcatgctgt tcccccaggt   1752
gttgtaacac aactttattg attgaatttt taagctactt attcatagtt ttatatcccc   1812
ctaaactacc tttttgttcc ccattcctta attgtattgt tttcccaagt gtaattatca   1872
tgcgttttat atcttcctaa taaggtgtgg tctgtttgtc tgaacaaagt gctagacttt   1932
ctggagtgat aatctggtga caaatattct ctctgtagct gtaagcaagt cacttaatct   1992
ttctacctct tttttctatc tgccaaattg agatatgat acttaaccag ttagaagagg    2052
tagtgtgaat attaattagt ttatattact ctcattcttt gaacatgaac tatgcctatg   2112
tagtgtcttt atttgctcag ctggctgaga cactgaagaa gtcactgaac aaaacctaca   2172
cacgtacctt catgtgattc actgccttcc tctctctacc agtctatttc cactgaacaa   2232
aacctacaca catacctttca tgtggttcag tgccttcctc tctctaccag tctatttcca  2292
ctgaacaaaa cctacgcaca taccttcatg tggctcagtg ccttcctctc tctaccagtc   2352
tatttccatt cttcagctg tgtctgacat gtttgtgctc tgttccattt taacaactgc    2412
tcttactttt ccagtctgta cagaatgcta tttcacttga gcaagatgat gtaatggaaa   2472
gggtgttggc attggtgtct ggagacctgg atttgagtct tggtgctatc aatcaccgtc   2532
tgtgtttgag caaggcattt ggctgctgta agcttattgc ttcatctgta agcggtggtt   2592
tgtaattcct gatcttccca cctcacagtg atgttgtggg gatccagtga gatagaatac   2652
atgtaagtgt ggttttgtaa tttaaaagt gctatactaa gggaaagaat tgaggaatta    2712
actgcatacg ttttggtgtt gcttttcaaa tgtttgaaaa caaaaaaaat gttaagaaat   2772
gggtttcttg ccttaaccag tctctcaagt gatgagacag tgaagtaaaa ttgagtgcac   2832
taaacaaata agattctgag gaagtcttat cttctgcagt gagtatggcc cgatgctttc   2892
tgtggctaaa cagatgtaat gggaagaaat aaaagcctac gtgttggtaa atccaacagc   2952
aagggagatt tttgaatcat aataactcat aaggtgctat ctgttcagtg atgccctcag   3012
agctcttgct gttagctggc agctgacgct gctaggatag ttagtttgga aatggtactt   3072
cataataaac tacacaagga aagtcagcca ctgtgtctta tgaggaattg gacctaataa   3132
attttagtgt gccttccaaa cctgagaata tatgcttttg gaagttaaaa tttaaatggc   3192
ttttgccaca tacatagatc ttcatgatgt gtgagtgtaa ttccatgtgg atatcagtta   3252
ccaaacatta caaaaaaatt ttatggccca aaatgaccaa cgaaattgtt acaatagaat   3312
ttatccaatt ttgatctttt tatattcttc taccacacct ggaaacagac caatagacat   3372
tttggggttt tataatagga atttgtataa agcattactc ttttcaata aattgttttt    3432
taatttaaaa aaggaaaaa aaaaaaaaa aaaaaaaaaa agggcggccg c               3483
```

FIG. 2B

```
gtcgacccac gcgtccggct ccgacaacct ttgcacgcgc acaaactacg gggacgattt    60
ctgattgatt tttggcgctt tcgatccacc ctcctccctt ctc atg gga ctt tgg   115
                                              Met Gly Leu Trp
                                                1 gga caa agc gtc ccg acc gcc tcg agc gct cga gca ggg cgc tat cca   163
Gly Gln Ser Val Pro Thr Ala Ser Ser Ala Arg Ala Gly Arg Tyr Pro
  5              10                  15                  20 gga gcc agg aca gcg tcg gga acc aga cca tgg ctc ctg gac tcc aag   211
Gly Ala Arg Thr Ala Ser Gly Thr Arg Pro Trp Leu Leu Asp Ser Lys
             25                  30                  35 atc ctt aag ttc gtc gtc ttc atc gtc gcg gtt ctg ctg ccg gtc cgg   259
Ile Leu Lys Phe Val Val Phe Ile Val Ala Val Leu Leu Pro Val Arg
         40                  45                  50 gtt gac tct gcc acc atc ccc cgg cag gac gaa gtt ccc cag cag aca   307
Val Asp Ser Ala Thr Ile Pro Arg Gln Asp Glu Val Pro Gln Gln Thr
     55                  60                  65 gtg gcc cca cag caa cag agg cgc agc ctc aag gag gag gag tgt cca   355
Val Ala Pro Gln Gln Gln Arg Arg Ser Leu Lys Glu Glu Glu Cys Pro
 70                  75                  80 gca gga tct cat aga tca gaa tat act gga gcc tgt aac ccg tgc aca   403
Ala Gly Ser His Arg Ser Glu Tyr Thr Gly Ala Cys Asn Pro Cys Thr
 85                  90                  95                 100 gag ggt gtg gat tac acc att gct tcc aac aat ttg cct tct tgc ctg   451
Glu Gly Val Asp Tyr Thr Ile Ala Ser Asn Asn Leu Pro Ser Cys Leu
                105                 110                 115 cta tgt aca gtt tgt aaa tca ggt caa aca aat aaa agt tcc tgt acc   499
Leu Cys Thr Val Cys Lys Ser Gly Gln Thr Asn Lys Ser Ser Cys Thr
            120                 125                 130 acg acc aga gac acc gtg tgt cag tgt gaa aaa gga agc ttc cag gat   547
Thr Thr Arg Asp Thr Val Cys Gln Cys Glu Lys Gly Ser Phe Gln Asp
        135                 140                 145 aaa aac tcc cct gag atg tgc cgg acg tgt aga aca ggg tgt ccc aga   595
Lys Asn Ser Pro Glu Met Cys Arg Thr Cys Arg Thr Gly Cys Pro Arg
150                 155                 160 ggg atg gtc aag gtc agt aat tgt acg ccc cgg agt gac atc aag tgc   643
Gly Met Val Lys Val Ser Asn Cys Thr Pro Arg Ser Asp Ile Lys Cys
165                 170                 175                 180 aaa aat gaa tca gct gcc agt tcc act ggg aaa acc cca gca gcg gag   691
Lys Asn Glu Ser Ala Ala Ser Ser Thr Gly Lys Thr Pro Ala Ala Glu
                185                 190                 195 gag aca gtg acc acc atc ctg ggg atg ctt gcc tct ccc tat cac tac   739
Glu Thr Val Thr Thr Ile Leu Gly Met Leu Ala Ser Pro Tyr His Tyr
            200                 205                 210 ctt atc atc ata gtg gtt tta gtc atc att tta gct gtg gtt gtg gtt   787
Leu Ile Ile Ile Val Val Leu Val Ile Ile Leu Ala Val Val Val Val
        215                 220                 225 ggc ttt tca tgt cgg aag aaa ttc att tct tac ctc aaa ggc atc tgc   835
Gly Phe Ser Cys Arg Lys Lys Phe Ile Ser Tyr Leu Lys Gly Ile Cys
    230                 235                 240 tca ggt ggt gga gga ggt ccc gaa cgt gtg cac aga gtc ctt ttc cgg   883
Ser Gly Gly Gly Gly Gly Pro Glu Arg Val His Arg Val Leu Phe Arg
245                 250                 255                 260 cgg cgt tca tgt cct tca cga gtt cct ggg gcg gag gac aat gcc cgc   931
Arg Arg Ser Cys Pro Ser Arg Val Pro Gly Ala Glu Asp Asn Ala Arg
                265                 270                 275
```

FIG. 3A

```
aac cag acc ctg agt aac aga tac ttg cag ccc acc cag gtc tct gag      979
Asn Glu Thr Leu Ser Asn Arg Tyr Leu Gln Pro Thr Gln Val Ser Glu
            280                 285                 290 cag gaa atc caa ggt cag gag ctg gca gag cta aca ggt gtg act gta     1027
Gln Glu Ile Gln Gly Gln Glu Leu Ala Glu Leu Thr Gly Val Thr Val
        295                 300                 305 gag tcg cca gag cag cca cag cgt ctg ctg gaa cag gca gaa gct gaa     1075
Glu Ser Pro Glu Gln Pro Gln Arg Leu Leu Glu Gln Ala Glu Ala Glu
        310                 315                 320 ggg tgt cag agg agg agg ctg ctg gtt cca gtg aat gac gct gac tcc     1123
Gly Cys Gln Arg Arg Arg Leu Leu Val Pro Val Asn Asp Ala Asp Ser
325                 330                 335                 340 gct gac atc agc acc ttg ctg gat gcc tcg gca aca ctg gaa gaa gga     1171
Ala Asp Ile Ser Thr Leu Leu Asp Ala Ser Ala Thr Leu Glu Glu Gly
                345                 350                 355 cat gca aag gaa aca att cag gac caa ctg gtg ggc tcc gaa aag ctc     1219
His Ala Lys Glu Thr Ile Gln Asp Gln Leu Val Gly Ser Glu Lys Leu
            360                 365                 370 ttt tat gaa gaa gat gaa gca ggc tct gct acg tcc tgc ctg             1261
Phe Tyr Glu Glu Asp Glu Ala Gly Ser Ala Thr Ser Cys Leu
        375                 380                 385 tgaaagaatc tcttcaggaa accagagctt ccctcattta ccttttctcc tacaaaggga   1321
agcagcctgg aagaaacagt ccagtacttg acccatgccc caacaaactc tactatccaa   1381
tatggggcag cttaccaatg gtcctagaac tttgttaacg cacttggagt aatttttatg   1441
aaatactgcg tgtgataagc aaacgggaga aatttatatc agattcttgg ctgcatagtt   1501
atacgattgt gtattaaggg tcgttttagg ccacatgcgg tggctcatgc ctgtaatccc   1561
agcactttga taggctgagg caggtggatt gcttgagctc gggagtttga gaccagcctc   1621
atcaacacag tgaaactcca tctcaattta aaaagaaaaa aagtggtttt aggatgtcat   1681
tctttgcagt tcttcatcat cagacaagtc ttttttttctg cttcttatat tgcaagctcc   1741
atctctactg gtgtgtgcat ttaatgacat ctaactacag atgccgcaca gccacaatgc   1801
tttgccttat aatttttttaa ctttagaacg ggattatctt gttattacct gtattttcag   1861
tttcggatat ttttgactta atgatgagat tatcaagacg tagccctatg ctaagtcatg   1921
agcatatgga cttacgaggg ttcgacttag agttttgagc tttaagatac gattattggg   1981
gcttacccc  accttaatta gagaaacatt tatattgctt actactgtag gctgtacatc   2041
tcttttccga tttttgtata atgatgtaaa catgaaaaaa ctttaggaaa tgcacttatt   2101
aggctgttta catgggttgc ctggatacaa atcagcagtc aaaaatgact aaaaatataa   2161
ctagtgacgg agggagaaat cctccctctg tgggaggcac ttactgcatt ccagttctcc   2221
ctcctgcgcc ctgagactgg accagggttt gatggctggc agcttctcaa ggggcagctt   2281
gtcttacttg taattttag  aggtatatag ccatatttat ttataaataa atatttattt   2341
atttatttat aagtagatgt ttacatatgc ccaggatttt gaagagcctg gtatctttgg   2401
gaagccatgt gtctggtttg tcgtgctggg acagtcatgg gactgcatct tccgacttgt   2461
ccacagcaga tgaggacagt cagaattaag ttagatccga gactgcgaag agcttctctt   2521
tcaagcgcca ttacagttga acgttagtga atcttgagcc tcatttgggc tcagggcaga   2581
gcaggtgttt atctgccccg gcatctgcca tggcatcaag agggaagagt ggacggtgct   2641
tgggaatggt gtgaaatggt tgccgactca ggcatggatg ggccctctc  gcttctggtg   2701
gtctgtgaac tgagtccctg ggatgccttt tagggcagag attcctgagc tgcgttttag   2761
ggtacagatt ccctgtttga ggagcttggc ccctctgtaa gcatctgact catctcagag   2821
atatcaattc ttaaacactg tgacaacagg atctaaaatg gctgagcttct ttgtccttgt   2881
gtcacgttcc attattttat ttaaaaacct cagtaatcgt tttagcttct ttccagcaaa   2941
ctcttctcca cagtagccca gtcgtggtag gataaattac ggatatagtc attctagggg   3001
tttcagtctt ttccatctca aggcattgtg tgttttgttc cgggactggt ttggctggga   3061
caaagttaga actgcctgaa gttcgcacat tcagattgtt gtgtccatgg agtttagga    3121
ggggatggcc tttccggtct tcgcacttcc atcctctccc acttccatct ggcgtcccac   3181
accttgtccc ctgcacttct ggatgacaca gggtgctgct gcctcctagt ctttgccttt   3241
gctgggcctt ctgtgcagga gacttggtct caaagctcag agagccag  tccggtccca   3301
gctcctttgt cccttcctca gaggccttcc ttgaagatgc atctagacta ccagccttat   3361
cagtgtttaa gcttattcct ttaacataag cttcctgaca acatgaaatt gttggggttt   3421
tttggcgttg gttgaattgt ttaggtttttg ctttataccc gggccaaata gcacataaca   3481
cctggttata tatgaaatac tcatatgttt atgaccaaaa taaatatgaa acctcatatt   3541
aaaaaaaaaa aaaaaaaagg gcggccgc                                      3569
```

FIG. 3B

```
gccttttagg gcagagattc ctgagctgcg ttttagggta cagattccct gtttgaggag   60
cttggcccct ctgtaagcat ctgactcatc tcagagatat caattcttaa acactgtgac  120
aacaggatct aaaatggctg acacatttgt ccttgtgtca cgttccatta ttttatttaa  180
aaacgtcagt aatcgtttta gcttctttcc agcaaactct tctccacagt agcccagtcg  240
tggtaggata aattacggat atagtcattc tagggtttc agtcttttcg atctcaaggc   300
attgtgtgtt ttgttccggg actggtttgg ctgggacaaa gttagaactg cctgaagttc  360
gcacattcag attgttgtgt ccatggagtt ttaggagggg atggcctttc cggtcttcgg  420
acttccatcc tctcccactt ccatctggcg tcccacacct tgtccctgc acttctggat   480
gacacagggt gctgctgcct cctagtcttt gcctttgctg ggccttctgt gcaggagact  540
tggtctcaaa gctcagagag agccagtccg gtcccagctc ctttgtccct tcctcagagg  600
ccttccttga agatgcatct agactaccag ccttatcagt gtttaagctt attcctttaa  660
cataagcttc ctgacaacat gaaattgttg gggttttttg gcgttggttg atttgtttag  720
gttttgcttt atacccgggc caaatagcac ataacacctg gttatatatg aaatactcat  780
atgtttatga ccaaaataaa tatgaaacct catattaaaa aaaaaaaaaa aaaagggcgg  840
ccg                                                                843
```

FIG. 4

```
Ala Ala Ala Thr Pro Ser Lys Val Trp Gly Ser Ser Ala Gly Arg Ile
 1           5                   10                  15
Glu Pro Arg Gly Gly Gly Arg Gly Ala Leu Pro Thr Ser Met Gly Gln
            20                  25                  30
His Gly Pro Ser Ala Arg Ala Arg Ala Gly Arg Ala Pro Gly Pro Arg
            35                  40                  45
Pro Ala Arg Glu Ala Ser Pro Arg Leu Arg Val His Lys Thr Phe Lys
 50                  55                  60
Phe Val Val Val Gly Val Leu Leu Gln Val Val Pro Ser Ser Ala Ala
 65                  70                  75                  80
Thr Ile Lys Leu His Asp Gln Ser Ile Gly Thr Gln Gln Trp Glu His
            85                  90                  95
Ser Pro Leu Gly Glu Leu Cys Pro Pro Gly Ser His Arg Ser Glu Arg
            100                 105                 110
Pro Gly Ala Cys Asn Arg Cys Thr Glu Gly Val Gly Tyr Thr Asn Ala
            115                 120                 125
Ser Asn Asn Leu Phe Ala Cys Leu Pro Cys Thr Ala Cys Lys Ser Asp
 130                 135                 140
Glu Glu Glu Arg Ser Pro Cys Thr Thr Thr Arg Asn Thr Ala Cys Gln
 145                 150                 155                 160
Cys Lys Pro Gly Thr Phe Arg Asn Asp Asn Ser Ala Glu Met Cys Arg
            165                 170                 175
Lys Cys Ser Thr Gly Cys Pro Arg Gly Met Val Lys Val Lys Asp Cys
            180                 185                 190
Thr Pro Trp Ser Asp Ile Glu Cys Val His Lys Glu Ser Gly Asn Gly
            195                 200                 205
His Asn Ile Trp Val Ile Leu Val Val Thr Leu Val Val Pro Leu Leu
 210                 215                 220
Leu Val Ala Val Leu Ile Val Cys Cys Cys
 225                 230
```

FIG. 5

| | | |
|---|---|---|
| gc gtc cgg aac aag acg ctg ccc tgg tct ccc tgc agt gct gtc tac<br>   Val Arg Asn Lys Thr Leu Pro Trp Ser Pro Cys Ser Ala Val Tyr<br>    1               5                 10             15 | | 47 |
| ctc acg gag ctc ctg gat gat ggt cac gga gac tgc ctc ctg gat gat<br>Leu Thr Glu Leu Leu Asp Asp Gly His Gly Asp Cys Leu Leu Asp Asp<br>            20                  25             30 | | 95 |
| ggc cac agc acc ctc tat gag ctg gac cag cag tgc aag cag atc ttt<br>Gly His Ser Thr Leu Tyr Glu Leu Asp Gln Gln Cys Lys Gln Ile Phe<br>        35                   40                 45 | | 143 |
| ggg cct gat ttc cga cac tgc ccc aac acc tct gtg gag gac atc tgt<br>Gly Pro Asp Phe Arg His Cys Pro Asn Thr Ser Val Glu Asp Ile Cys<br>           50                  55             60 | | 191 |
| gtc cag ctc tgg tgc cgt cat cgg gat agt gat gag ccc att tgc cac<br>Val Gln Leu Trp Cys Arg His Arg Asp Ser Asp Glu Pro Ile Cys His<br>    65                   70                 75 | | 239 |
| aca aag aat gcc agc ttg ctc tgg gct gat ggt acg ccc tgt ggc cct<br>Thr Lys Asn Ala Ser Leu Leu Trp Ala Asp Gly Thr Pro Cys Gly Pro<br> 80               85                90             95 | | 287 |
| ggg cac ctg tgc ctg gat ggt agc tgt gtg ctc cgg gag gaa gta gag<br>Gly His Leu Cys Leu Asp Gly Ser Cys Val Leu Arg Glu Glu Val Glu<br>           100                105            110 | | 335 |
| aat ccc aag gct gtg gta gat gga gac tgg ggt ccc tgg gga ccc tgg<br>Asn Pro Lys Ala Val Val Asp Gly Asp Trp Gly Pro Trp Gly Pro Trp<br>         115                120            125 | | 383 |
| gga caa tgt tct cgc acc tgt ggt gga ggg ata cag ttt tcg aac cgt<br>Gly Gln Cys Ser Arg Thr Cys Gly Gly Gly Ile Gln Phe Ser Asn Arg<br>        130                135            140 | | 431 |
| gag tgt gat aat cca gca cct cag aat gga gga aga ttt tgc ctg gga<br>Glu Cys Asp Asn Pro Ala Pro Gln Asn Gly Gly Arg Phe Cys Leu Gly<br> 145                150                155 | | 479 |
| gag aga gtc aag tac caa tct tgc aag aca gag gaa tgt cca cca aat<br>Glu Arg Val Lys Tyr Gln Ser Cys Lys Thr Glu Glu Cys Pro Pro Asn<br>160                165              170            175 | | 527 |
| gga aaa agc ttc agg gag cag cag tgt gaa aaa tat aat gcc tac aac<br>Gly Lys Ser Phe Arg Glu Gln Gln Cys Glu Lys Tyr Asn Ala Tyr Asn<br>             180                185           190 | | 575 |
| cac acg gac ctg gat ggg aat ttc ctt cag tgg gtc ccc aaa tac tca<br>His Thr Asp Leu Asp Gly Asn Phe Leu Gln Trp Val Pro Lys Tyr Ser<br>          195                200            205 | | 623 |

FIG. 6A

```
gga gtg tcc ccc cga gac cga tgc aaa ctg ttt tgc aga gcc cgt ggg      671
Gly Val Ser Pro Arg Asp Arg Cys Lys Leu Phe Cys Arg Ala Arg Gly
        210                 215                 220 agg agt gag ttc aaa gtg ttt caa act aag gtg atc cat ggc act ctg      719
Arg Ser Glu Phe Lys Val Phe Gln Thr Lys Val Ile Asp Gly Thr Leu
    225                 230                 235 tgc gga ccg gat act ctg gcc atc tgt gtg cgg gga cag tgc gtt aag      767
Cys Gly Pro Asp Thr Leu Ala Ile Cys Val Arg Gly Gln Cys Val Lys
240                 245                 250                 255 gct ggc tgt gac cat gtg gtg aac tca cct aag aag ctg gac aag tgt      815
Ala Gly Cys Asp His Val Val Asn Ser Pro Lys Lys Leu Asp Lys Cys
                260                 265                 270 ggg gtg tgt ggg ggc aaa ggc act gcc tgt agg aag gtc tca ggt tct      863
Gly Val Cys Gly Gly Lys Gly Thr Ala Cys Arg Lys Val Ser Gly Ser
            275                 280                 285 ttc acc ccc ttc agt tat ggc tac aat gac att gtc acc atc cca gct      911
Phe Thr Pro Phe Ser Tyr Gly Tyr Asn Asp Ile Val Thr Ile Pro Ala
        290                 295                 300 ggt gcc aca aat att gat gtg aaa caa cgg agc cac cca ggg gtc cag      959
Gly Ala Thr Asn Ile Asp Val Lys Gln Arg Ser His Pro Gly Val Gln
    305                 310                 315 aat gac ggc agc tac ctg gca ctg aag aca gcc aat cgg cag tac ctg     1007
Asn Asp Gly Ser Tyr Leu Ala Leu Lys Thr Ala Asn Gly Gln Tyr Leu
320                 325                 330                 335 ctc aat ggt aac cta gcc atc tct gcc ata gag caa gac atc ttg atg     1055
Leu Asn Gly Asn Leu Ala Ile Ser Ala Ile Glu Gln Asp Ile Leu Met
                340                 345                 350 aag ggg acc atc cta aag tac agt ggt tcc atg gcc acc ctg gag cgg     1103
Lys Gly Thr Ile Leu Lys Tyr Ser Gly Ser Met Ala Thr Leu Glu Arg
            355                 360                 365 ctg cag agc ttc caa gcc ctc cct gag cct ctt aca gta cag ctc ctg     1151
Leu Gln Ser Phe Gln Ala Leu Pro Glu Pro Leu Thr Val Gln Leu Leu
        370                 375                 380 act gtg tct ggt gag gtc ttc cct cca aaa gtc aaa tat acc ttc ttc     1199
Thr Val Ser Gly Glu Val Phe Pro Pro Lys Val Lys Tyr Thr Phe Phe
    385                 390                 395 gtc ccc aat gac acg gac ttc aac gtg cag agt agc aaa gaa aga gca     1247
Val Pro Asn Asp Thr Asp Phe Asn Val Gln Ser Ser Lys Glu Arg Ala
400                 405                 410                 415 agc acc aac atc att cag tcc ttg ccc tat gca gag tgg gtg ctg ggg     1295
Ser Thr Asn Ile Ile Gln Ser Leu Pro Tyr Ala Glu Trp Val Leu Gly
                420                 425                 430 gac tgg tct gaa tgt cca agc aca tgt gga ggt ggc tgg cag cgg cgg     1343
Asp Trp Ser Glu Cys Pro Ser Thr Cys Gly Gly Gly Trp Gln Arg Arg
            435                 440                 445
```

FIG. 6B

```
act gtg gaa tgc agg gac ccc tca ggt cag gcc tct gac acc tgt gat    1391
Thr Val Glu Cys Arg Asp Pro Ser Gly Gln Ala Ser Asp Thr Cys Asp
        450                 455                 460 gag gct ctg aaa cct gag gat gcc aag ccc tgt gga agc cag cca tgt    1439
Glu Ala Leu Lys Pro Glu Asp Ala Lys Pro Cys Gly Ser Gln Pro Cys
    465                 470                 475 ctc ctc tgatcccctt ggtggacatg tctaaggctt atggatttgg gctactggcg    1495
Leu Leu
480 tacagacaaa ggtctcctct gaggtgacac tacatatcaa gatggcatgg cccttccagg    1555
ccttctatta ctacaaccct ttgggtacca cctaattcat aaggaagaga gaagaggatg    1615
taagggtaac agactgtaaa gttgactgtc tagtggactg gaccttgttt atgaccaaga    1675
agatgggata ggttaaaagg taaagtgtg cttattgatc caaaggtgag atttcagaac    1735
cagcctcttt gcaaggact agaaaggtta aatgagaaag aagaatttt tttctctttg    1795
gtttctccaa taatcaatct acctcacagc cggaggaact tggtgtataa ggccaggtgt    1855
tagtggtgag tgccaaggca ctctccatag atatcttcga gccatcttca gaaatggcca    1915
tggctgtttt cagtattaaa actctgttgt ctcaaaaggt ggtggtgtcc atcacagggt    1975
tatagaaagc cacttgttct caggctgcct cctgctgggg cggacccctt tcaagtattt    2035
atgcaaatat gtttctgaac taaagtgtga tcttacacca aaaaaaaaaa aaaaaaaaa    2095
aaaaaaaaaa ggcggccgc                                              2114
```

FIG. 6C

```
gtcgacccac gcgtccgggg caagcttgcc agcagatctg cagctgccaa aatggggcag    60
actgtgacag tgtgactgga aagtgcacct gtgcccagg attcaaagga attgactgct   120
ctaccccatg ccctctggga acctatggga taaactgttc ctctcgctgt ggctgtaaaa   180
atgatgcagt ctgctctcct gtggacgggt cttgtacttg caaggcaggc tggcacgggg   240
tggactgctc catcagatgt cccagtggca catgggctt tggctgtaac ttaacatgcc    300
agtgcctcaa cggggagcc tgcaacaccc tggacgggac ctgcacgtgt gcacctggat    360
ggcgcgggga caaatgcgaa cttccctgcc acgatggcac gtacgggctg aactgtgctg   420
agcgctgcga ctgcagccac gcagatggct gccaccctac cacgggccat tgccgctgcc   480
tccccggatg gtcaggtgtc cactgtgaca gcgtgtgtgc tgagggacgc tggggcccca   540
actgctccct gcctgctac tgtaaaaatg gggcttcatg ctcccctgat gatggcatct    600
gcgagtgtgc accaggcttc cgaggcacca cttgtcagag gatctgctcc cctggttttt   660
atgggcatcg ctgcagccag acatgcccac agtgcgttca cagcagcggg ccctgccacc   720
acatcaccgg cctgtgtgac tgcttgcctg gcttcacagg cgccctctgc aatgaagtgt    780
gtcccagtgg cagatttggg aaaaactgtg caggaatttg tacctgcacc aacaacggaa   840
cctgtaaccc cattgacaga tcttgtcagt gttaccccgg ttggattggc agtgactgct   900
ctcaaccatg tccacctgcc cactgggcc caaactgcat ccacacgtgc aactgccata    960
atggagcttt ctgcagcgcc tacgatgggg aatgtaaatg cactcctggc tggacagggc   1020
tctactgcac tcagagatgt cctctagggt tttatggaaa agattgtgca ctgatatgcc   1080
aatgtcaaaa cggagctgac tgcgaccaca tttctgggca gtgtacttgc cgcactggat   1140
tcatgggacg gcactgtgag cagaagtgcc cttcaggaac atatggctat ggctgtcgcc   1200
agatatgtga ttgtctgaac aactccacct gcgaccacat cactgggacc tgttactgca   1260
gccccggatg gaagggagcg agatgtgatc aagctggtgt tatcatagtt ggaaatctga   1320
acagcttaag ccgaaccagt actgctctcc ctgctgattc ctaccaaatc ggggccattg   1380
caggcatcat cattcttgtc ctagttgttc tcttcctact ggcattgttc attatttata   1440
gacacagc                                                           1448
```

FIG. 7

```
nagcccaaca ggaatgttct atgaaagtga acctaacagt gagtgttgtt cccaaggagt    60
attcagcaat aatggcgtc tntcccaagg atccatatga cctcccaaag aacagtcaca   120
tcccttgtca ttatgacctg ctgccagtcc gagacagttc atcctcccct aagcaagagg   180
acagtggagg tagcagcagc aacagcagca gcagcagtga atgacaccaa aggaccgctt   240
ggtagccact ggaacccttt ccagaactgc tgtttggttc ttctccatcc tcaattttgc   300
cactttcatg tgaatgttag tcaattcggt gggcaatttt tggacatgaa ccagaaagct   360
gaaagctgag gctgacacgg actgtaggtg ctttttgttc aggtggattc gaaggagtta   420
gagatgtgat ttgccattgc tgttagtttt agaactatac ccgtgaagca tgacttattg   480
taagatgttg gctgaaagca tgaacttgca gaactccctc ggagacgcag gttgcagtgg   540
acattgggat tgttgcttga aaaattaaaa tttgaatatt ttctctctca tttgcatcat   600
agagctctac ctaggattgt acagtttacc ataaaattta cttcatgaaa gtgggaatca   660
ctgaacatgt agaagacaag gaacatattg ttaactcctg attcttaact ttattcaact   720
ggactcagaa ttgtagggat aatatgaatg caggaggaaa cattctgtca ggcggtatga   780
ctggacagaa tttgaatata ctctaaaagt ggacagaaaa tttacgaaaa tcttagattt   840
tgtttagaat gagaaaatat acaattagaa ttattttaga aatagtagga agtattgcag   900
aagtcaatac acaaatgtgc caggcagagg tggttttctc tgtttgactc tcaaccaact   960
tcagatctat gacattattc tgatcactgg ctccatcata catattcacc acttgagatt   1020
cataacatat caatagttat ttcataaata tagaatgaa ataatttat ttttgacaga    1080
ctggatggaa tgagtgtgta atgattgata aaggttgtaa atttaaatg caagatgacg   1140
cttacgttct gtaaaccatt agtaatacat gctgtaatat agaattagtg gaacattttg   1200
attaatcttt ccctagaagt gactgaaata ttttgtgca tatttgagaa agggaacttt    1260
ccttttatta attgtcaatt tagagaaact atgcttaagc tggtcttttg cattgctaat   1320
gtgacatgta cccaactttt cattaatttg tatttccatt ttaaattgc atattctatg    1380
ttttgtagtg tttggattgt taatgaaaaa atattatatg ttcgttattc cttgtattat   1440
tgccacttat cttttgcttg ataaaaatgc gttgttcttt tttcttttgg agggacaaga   1500
tgaaaatata aatttgaat tgattaaaat tggtcgttac taaaatagta tagtaaaaaa   1560
aaaaaaaaag ggcggccg                                                1578
```

FIG. 8

```
Thr Arg Pro Ile Leu Val Ile His Asp Glu Gln Lys Gly Pro Glu Val
 1           5                  10                 15
Thr Ser Asn Ala Ala Leu Thr Leu Arg Asn Phe Cys Asn Trp Gln Lys
            20                  25                 30
Gln His Asn Pro Pro Ser Asp Arg Asp Ala Glu His Tyr Asp Thr Ala
            35                  40                 45
Ile Leu Phe Thr Arg Gln Asp Leu Cys Gly Ser Gln Thr Cys Asp Thr
     50                  55                 60
Leu Gly Met Ala Asp Val Gly Thr Val Cys Asp Pro Ser Arg Ser Cys
 65                  70                 75                  80
Ser Val Ile Glu Asp Asp Gly Leu Gln Ala Ala Phe Thr Thr Ala His
                 85                  90                 95
Glu Leu Gly His Val Phe Asn Met Pro His Asp Asp Ala Lys Gln Cys
            100                 105                110
Ala Ser Leu Asn Gly Val Asn Gln Asp Ser His Met Met Ala Ser Met
            115                 120                125
Leu Ser Asn Leu Asp His Ser Gln Pro Trp Ser Pro Cys Ser Ala Tyr
    130                 135                140
```

FIG. 9A

```
Met Ile Thr Ser Phe Leu Asp Asn Gly His Gly Glu Cys Leu Met Asp
145                 150                 155                 160
Lys Pro Gln Asn Pro Ile Gln Leu Pro Gly Asp Leu Pro Gly Thr Ser
                165                 170                 175
Tyr Asp Ala Asn Arg Gln Cys Gln Phe Thr Phe Gly Glu Asp Ser Lys
            180                 185                 190
His Cys Pro Asp Ala Ala Ser Thr Cys Ser Thr Leu Trp Cys Thr Gly
        195                 200                 205
Thr Ser Gly Gly Val Leu Val Cys Gln Thr Lys His Phe Pro Trp Ala
    210                 215                 220
Asp Gly Thr Ser Cys Gly Glu Gly Lys Trp Cys Ile Asn Gly Lys Cys
225                 230                 235                 240
Val Asn Lys Thr Asp Arg Lys His Phe Asp Thr Pro Phe His Gly Ser
                245                 250                 255
Trp Gly Met Trp Gly Pro Trp Gly Asp Cys Ser Arg Thr Cys Gly Gly
            260                 265                 270
Gly Val Gln Tyr Thr Met Arg Glu Cys Asp Asn Pro Val Pro Lys Asn
        275                 280                 285
Gly Gly Lys Tyr Cys Glu Gly Lys Arg Val Arg Tyr Arg Ser Cys Asn
    290                 295                 300
Leu Glu Asp Cys Pro Asp Asn Asn Gly Lys Thr Phe Arg Glu Glu Gln
305                 310                 315                 320
Cys Glu Ala His Asn Glu Phe Ser Lys Ala Ser Phe Gly Ser Gly Pro
                325                 330                 335
Ala Val Glu Trp Ile Pro Lys Tyr Ala Gly Val Ser Pro Lys Asp Arg
            340                 345                 350
Cys Lys Leu Ile Cys Gln Ala Lys Gly Ile Gly Tyr Phe Phe Val Leu
        355                 360                 365
Gln Pro Lys Val Val Asp Gly Thr Pro Cys Ser Pro Asp Ser Thr Ser
    370                 375                 380
Val Cys Val Gln Gly Gln Cys Val Lys Ala Gly Cys Asp Arg Ile Ile
385                 390                 395                 400
Asp Ser Lys Lys Lys Phe Asp Lys Cys Gly Val Cys Gly Gly Asn Gly
                405                 410                 415
Ser Thr Cys Lys Lys Ile Ser Gly Ser Val Thr Ser Ala Lys Pro Gly
            420                 425                 430
Tyr His Asp Ile Ile Thr Ile Pro Ile Gly Ala Thr Asn Ile Glu Val
        435                 440                 445
Lys Gln Arg Asn Gln Arg Gly Ser Arg Asn Asn Gly Ser Phe Leu Ala
    450                 455                 460
Ile Lys Ala Ala Asp Gly Thr Tyr Ile Leu Asn Gly Asp Tyr Thr Leu
465                 470                 475                 480
Ser Thr Leu Glu Gln Asp Ile Met Tyr Lys Gly Val Val Leu Arg Tyr
                485                 490                 495
Ser Gly Ser Ser Ala Ala Leu Glu Arg Ile Arg Ser Phe Ser Pro Leu
            500                 505                 510
Lys Glu Pro Leu Thr Ile Gln Val Leu Thr Val Gly Asn Ala Leu Arg
        515                 520                 525
Pro Lys Ile Lys Tyr Thr Tyr Phe Val Lys Lys Lys Glu Ser Phe
    530                 535                 540
Asn Ala Ile Pro Thr Phe Ser Ala Trp Val Ile Glu Glu Trp Gly Glu
545                 550                 555                 560
Cys Ser Lys Thr Cys Gly Lys Gly Tyr Lys Lys Arg Ser Leu Lys Cys
                565                 570                 575
Leu Ser His Asp Gly Gly Val Leu Ser His Glu Ser Cys Asp Pro Leu
            580                 585                 590
Lys Lys Pro Lys His Phe Ile Asp Phe Cys Thr Met Ala Glu Cys Ser
        595                 600                 605
```

FIG. 9B

Met Gly Ser Ala Ala Leu Glu Ile Leu Gly Leu Val Leu Cys Leu Val
1           5               10              15
Gly Trp Gly Gly Leu Ile Leu Ala Cys Gly Leu Pro Met Trp Gln Val
        20              25              30
Thr Ala Phe Leu Asp His Asn Ile Val Thr Ala Gln Thr Thr Trp Lys
        35              40              45
Gly Leu Trp Met Ser Cys Val Val Gln Ser Thr Gly His Met Gln Cys
50              55              60
Lys Val Tyr Asp Ser Val Leu Ala Leu Ser Thr Glu Val Gln Ala Ala
65              70              75              80
Arg Ala Leu Thr Val Ser Ala Val Leu Leu Ala Phe Val Ala Leu Phe
            85              90              95
Val Thr Leu Ala Gly Ala Gln Cys Thr Thr Cys Val Ala Pro Gly Pro
            100             105             110
Ala Lys Ala Arg Val Ala Leu Thr Gly Gly Val Leu Tyr Leu Phe Cys
        115             120             125
Gly Leu Leu Ala Leu Val Pro Leu Cys Trp Phe Ala Asn Ile Val Val
130             135             140
Arg Glu Phe Tyr Asp Pro Ser Val Pro Val Ser Gln Lys Tyr Glu Leu
145             150             155             160
Gly Ala Ala Leu Tyr Ile Gly Trp Ala Ala Thr Ala Leu Leu Met Val
            165             170             175
Gly Gly Cys Leu Leu Cys Cys Gly Ala Trp Val Cys Thr Gly Arg Pro
            180             185             190
Asp Leu Ser Phe Pro Val Lys Tyr Ser Ala Pro Arg Arg Pro Thr Ala
        195             200             205
Thr Gly Asp Tyr Asp Lys Lys Asn Tyr Val
210             215

FIG. 10

Met Ser Met Ser Leu Glu Ile Thr Gly Thr Ser Leu Ala Val Leu Gly
1           5               10              15
Trp Leu Cys Thr Ile Val Cys Cys Ala Leu Pro Met Trp Arg Val Ser
        20              25              30
Ala Phe Ile Gly Ser Ser Ile Ile Thr Ala Gln Ile Thr Trp Glu Gly
        35              40              45
Leu Trp Met Asn Cys Val Gln Ser Thr Gly Gln Met Gln Cys Lys Met
50              55              60
Tyr Asp Ser Leu Leu Ala Leu Pro Gln Asp Leu Gln Ala Ala Arg Ala
65              70              75              80
Leu Ile Val Val Ser Ile Leu Leu Ala Ala Phe Gly Leu Leu Val Ala
            85              90              95
Leu Val Gly Ala Gln Cys Thr Asn Cys Val Gln Asp Glu Thr Ala Lys
            100             105             110
Ala Lys Ile Thr Ile Val Ala Gly Val Leu Phe Leu Leu Ala Ala Val
        115             120             125
Leu Thr Leu Val Pro Val Ser Trp Ser Ala Asn Thr Ile Ile Arg Asp
130             135             140
Phe Tyr Asn Pro Leu Val Pro Glu Ala Gln Lys Arg Glu Met Gly Thr
145             150             155             160
Gly Leu Tyr Val Gly Trp Ala Ala Ala Ala Leu Gln Leu Leu Gly Gly
            165             170             175
Ala Leu Leu Cys Cys Ser Cys Pro Pro Arg Glu Lys Tyr Ala Pro Thr
            180             185             190
Lys Ile Leu Tyr Ser Ala Pro Arg Ser Thr Gly Pro Gly Thr Gly Thr
        195             200             205
Gly Thr Ala Tyr Asp Arg Lys Thr Thr Ser Glu Arg Pro Gly Ala Arg
        210             215             220
Thr Pro His His His His Tyr Gln Pro Ser Met Tyr Pro Thr Arg Pro
225             230             235             240
Ala Cys Ser Leu Ala Ser Glu
            245

FIG. 11

```
  1 ....................VRNKTLPWSPCSAVYLTELLDDGHGDCLLDD  31
                          :.. ||||||| :|.:||:|||:||:|.
401 CASLNGVSGDSHLMASMLSSLDHSQPWSPCSAYMVTSFLDNGHGECLMDK 450

32 GH.........STLYELDQQCKQIFGPDFRHCPNTSVEDICVQLWCRHR  71
    :          :|||: :.||. .||.: :|||:.. ..|. |||
451 PQNPIKLPSDLPGTLYDANRQCQFTFGEESKHCPDAA...STCTTLWCTGT 498

72 DSDEPICHTKNGSLLWADGTPCGPGHLCLDGSCVLREEVENPKAVVDGDW 121
    .::  :|:||: : |||||.||.|.:|:.|.|| :.::.:  ..|.|.|
499 SGGLLVCQTKH..FPWADGTSCGEGKWCVSGKCVNKTDMKHFATPVHGSW 546
                                              ―――――→
122 GPWGPWGQCSRTCGGGIQFSNRECDNPAPQNGGRFCLGERVKYQSCKTEE 171
    |||||||:|||||||||:|:. ||||||.|.|||::| |.||:|.||..|:
547 GPWGPWGDCSRTCGGGVQYTMRECDNPVPKNGGKYCEGKRVRYRSCNIED 596
    ←――――――――――――――――――――――――――――――――――――――――――――――→
172 CPP.NGKSFREQQCEKYNAYNHTDLGN.FLQWVPKYSGVSPRDRCKLFC 219
    ||. |||.|||:||| .|.:......:.: ::|.|||.||||:||||| |
597 CPDNNGKTFREEQCEAHNEFSKASFGNEPTVEWTPKYAGVSPKDRCKLTC 646
    ←
220 RARGRSEFKVFETKVIDGTLCGPDTLAICVRGQCVKAGCDHVVNSPKKLD 269
    |:|  :  | |::.||:||| |:||. ..:||.||||||||||::::|.||:|
647 EAKGIGYFFVLQPKVVDGTPCSPDSTSVCVQGQCVKAGCDRIIDSKKKFD 696

270 KCGVCGGKGTACRKVSGSFTPFSYGYNDIVTIPAGATNIDVKQRSHPGVQ 319
    |||||||.|..|:|:|| .|. . ||:|||||||||||||:||||.:..| .
697 KCGVCGGNGSTCKKMSGIVTSTRPGYHDIVTIPAGATNIEVKHRNQRGSR 746

320 NDGSYLALKTANGQYLLNGNLAISAIEQDILMKGTILKYSGSMATLERLQ 369
    |:||:||::.|:| |:||||:..:|.:||: |||:|:|||| |.|||:.
747 NNGSFLAIRAADGTYIILNGNFTLSTLEQDLTYKGTVLRYSGSSAALERIR 796

370 SFQALPEPLTVQLLTVSGEVFPPKVKYTFFVPNDTDFNVQSSKERASTNI 419
    || :|.||||:|:|   |...:.||:|:|:|:|...|:           | |
797 SFSPLYEPLTIQVLMV.GHALRPKIKFTYFMKKKTE..........SFNA 835

420 IQSLPYAEWVLGDWSECPSTCGGGWQRRTVECRDPSGQASDTCDEALKPE 469
    |.  .::.|||:::|:||..|||:|||||.|||  .|:::...|...:||.
836 IP..TFSEWVIEEWGECSKTCGSGWQRRVVQCRDINGHPASECAKEVKPA 883
                                                     ――→
470 DAKPCGSQPC..LL*SPWWTCLRLMDLGY.WRTDKGLL*GDTTYQDGMAL 516
    ..:|||:. || : :.|..|.:  : || .|| |.:  ::...:: .
884 STRPCADLPCPHWQVGDWSPCSKTCGKGYKKRTLKCVSHDGGVLSNESCD 933
    ←―――――――――  ―――――――――――――――――――――――――――――――――――――
517 PGLLLLQPFGYHLIHKEERRGCKGNRL*S*LSSGLDLVYDQEDGIG*KVK 566
    |         : ::: :.  . .
934 PLKKPKHYIDFCTLTQCS............................. 951
    ←―――――――――――――――
```

FIG. 12

TANGO 71 NUCLEIC ACIDS

CROSS REFERENCE TO RELATED APPLICATIONS

This application claims priority from U.S. Ser. No. 60/054,966, filed Aug. 6, 1997 and U.S. Ser. No. 60/058,108, filed Sep. 5, 1997.

SUMMARY OF THE INVENTION

The invention relates to the discovery and characterization of Tango-71, Tango-73, Tango-74, Tango-76, and Tango-83. Tango-71 is a human protein which is approximately 90% identical to murine ADAMTS-1. Tango-73is a human protein that is 48% identical to rate RVP.1 (Briehl et al., *Mol. Endocrinol.* 5:1381, 1991). Tango-74 is a human protein with homology to TRAIL receptor (Pan et al., *Science* 276:111, 1997). Tango-76 is a rat protein which is approximately 40% identical to murine ADAMTS-1. Tango-83 is expressed by stimulated human astrocytes.

The invention features isolated nucleic acid molecules encoding Tango-71, Tango-73, Tango-74, Tango-76, or Tango-83 polypeptides; isolated nucleic acid molecules encoding polypeptides which are substantially similar to Tango-71, Tango-73, Tango-74, Tango-76, or Tango-83; and isolated nucleic acid molecules which hybridize under stringent conditions to a nucleic acid molecule having the sequence of the protein coding portion of SEQ ID NO:1, SEQ ID NO:3, SEQ ID NO:5, SEQ ID NO:7, or SEQ ID NO:9.

The invention also features a host cell which includes an isolated nucleic acid molecule encoding Tango-71, Tango-73, Tango-74, Tango-76, or Tango-83 and a nucleic acid vector (e.g., an expression vector; a vector which includes a regulatory element; a vector which includes a regulatory element selected from the group consisting of the cytomegalovirus hCMV immediate early gene, the early promoter of SV40 adenovirus, the late promoter of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors; vector which includes a regulatory element which directs tissue-specific expression; a vector which includes a reporter gene; a vector which includes a reporter gene selected from the group selected from the group consisting of β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT); a vector that is a plasmid, a vector that is a virus; and a vector that is a retrovirus) containing an isolated nucleic acid molecule encoding Tango-71, Tango-73, Tango-74, Tango-76, or Tango-83.

The invention also features substantially pure Tango-71, Tango-73, Tango-74, Tango-76, and Tango-83 polypeptides; a substantially pure polypeptide which includes a first portion and a second portion, the first portion including a Tango-71, Tango-73, Tango-74, Tango-76, or Tango-83 polypeptide and the second portion including a detectable marker.

The invention also features an antibody that selectively binds to a Tango-71, Tango-73, Tango-74, Tango-76, or Tango-83 polypeptide (e.g., a monoclonal antibody).

The invention also features a pharmaceutical composition which includes a Tango-71, Tango-73, Tango-74, Tango-76, or Tango-83 polypeptide.

The invention includes methods for diagnosing a disorder associated with aberrant expression of a protein of the invention (i.e., Tango-71, Tango-73, Tango-74, Tango-76, or Tango-83), the method including obtaining a biological sample from a patient and measuring the expression of the protein in the biological sample, wherein increased or decreased expression of the protein in the biological sample compared to a control indicates that the patient suffers from a disorder associated with aberrant expression of the protein.

The invention encompasses isolated nucleic acid molecules encoding Tango-71, Tango-73, Tango-74, Tango-76, or Tango-83 or a polypeptide fragment thereof; vectors containing these nucleic acid molecules; cells harboring recombinant DNA encoding Tango-71, Tango-73, Tango-74, Tango-76, or Tango-83; fusion proteins which include all or a portion of Tango-71, Tango-73, Tango-74, Tango-76, or Tango-83; transgenic animals which express Tango-71, Tango-73, Tango-74, Tango-76, or Tango-83; and recombinant knock-out animals which fail to express Tango-71, Tango-73, Tango-74, Tango-76, or Tango-83.

The invention encompasses nucleic acids that have a sequence that is substantially identical to a Tango-71, Tango-73, Tango-74, Tango-76, or Tango-83 nucleic acid sequence. A nucleic acid molecule which is substantially identical to a given reference nucleic acid molecule is hereby defined as a nucleic acid molecule having a sequence that has at least 85%, preferably 90%, and more preferably 95%, 98%, 99% or more identity to the sequence of the given reference nucleic acid molecule.

The invention also includes polypeptides which are substantially identical to Tango-71, Tango-73, Tango-74, Tango-76, or Tango-83 (e.g., polypeptides that are substantially identical to the polypeptide of SEQ ID NO:2, SEQ ID NO:4, SEQ ID NO:6, SEQ ID NO:8, or SEQ ID NO:10).

A polypeptide which is "substantially identical" to a given reference polypeptide molecule is a polypeptide having an amino acid sequence that has at least 85%, preferably 90%, and more preferably 95%, 98%, 99% or more identity to the amino acid sequence of the given reference polypeptide.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to Tango-71, Tango-73, Tango-74, Tango-76, or Tango-83 nucleic acid molecules of the invention. BLAST protein searches can be performed with the XBLAST program, score=50, wordlength=3 to obtain amino acid sequences homologous to Tango-71, Tango-73, Tango-74, Tango-76, or Tango-83 protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The nucleic acid molecules of the invention can be inserted into vectors, as described below, which will facilitate expression of the insert. The nucleic acid molecules and the polypeptides they encode can be used directly as diagnostic or therapeutic agents, or (in the case of a polypeptide) can be used to generate antibodies that, in turn, are therapeutically useful. Accordingly, expression vectors containing the nucleic acid molecules of invention, cells transfected with these vectors, the polypeptides expressed, and antibodies generated, against either the entire polypeptide or an antigenic fragment thereof, are among the preferred embodiments.

A transformed cell is any cell into which (or into ancestor of which) has been introduced, by means of recombinant DNA techniques, a nucleic acid encoding a polypeptide of the invention (e.g., a Tango-71, Tango-73, Tango-74, Tango-76, or Tango-83 polypeptide).

An isolated nucleic acid molecule is a nucleic acid molecule that is separated from the 5' and 3' coding sequences with which it is immediately contiguous in the naturally occurring genome of an organism. Isolated nucleic acid molecules include nucleic acid molecule which are not naturally occurring, e.g., nucleic acid molecules created by recombinant DNA techniques.

Nucleic acid molecules include both RNA and DNA, including cDNA, genomic DNA, and synthetic (e.g., chemically synthesized) DNA. Where single-stranded, the nucleic acid molecule may be a sense strand or an antisense strand.

The invention also encompasses nucleic acid molecules that hybridize, preferably under stringent conditions, to a nucleic acid molecule encoding a Tango-71, Tango-73, Tango-74, Tango-76, or Tango-83 polypeptide (e.g., a nucleic acid molecule having the sequence shown in SEQ ID NO:1, 3, 5, 7, or 9). Preferably the hybridizing nucleic acid molecule consists of 400, more preferably 200 nucleotides. Preferred hybridizing nucleic acid molecules have a biological activity possessed by Tango-71, Tango-73, Tango-74, Tango-76, or Tango-83.

The invention also features substantially pure or isolated Tango-71, Tango-73, Tango-74, Tango-76, or Tango-83 polypeptides, including those that correspond to various functional domains of Tango-71, Tango-73, Tango-74, Tango-76, or Tango-83, or fragments thereof.

The polypeptides of the invention can be produced recombinantly, chemically synthesized, or purified from tissues in which they are naturally expressed, according to standard biochemical methods of purification.

Also included in the invention are functional polypeptides, which possess one or more of the biological functions or activities of Tango-71, Tango-73, Tango-74, Tango-76, or Tango-83. These functions include the ability to bind some or all of the proteins which normally bind to Tango-71, Tango-73, Tango-74, Tango-76, or Tango-83. A functional polypeptide is also considered within the scope of the invention if it serves as an antigen for production of antibodies that specifically bind to Tango-71, Tango-73, Tango-74, Tango-76, or Tango-83. In many cases, functional polypeptides retain one or more domains present in the naturally-occurring form of the polypeptide.

The functional polypeptides may contain a primary amino acid sequence that has been modified from those disclosed herein. Preferably these modifications consist of conservative amino acid substitutions, as described herein.

The terms "protein" and "polypeptide" are used herein to describe any chain of amino acids, regardless of length or post-translational modification (for example, glycosylation or phosphorylation). Thus, the term "Tango-71, Tango-73, Tango-74, Tango-76, or Tango-83 polypeptides" includes full-length, naturally occurring Tango-71, Tango-73, Tango-74, Tango-76, or Tango-83 protein, as well a recombinantly or synthetically produced polypeptide that correspond to a full-length naturally occurring Tango-71, Tango-73, Tango-74, Tango-76, or Tango-83 protein or to particular domains or portions of a naturally occurring protein. The term also encompasses mature Tango-71, Tango-73, Tango-74, Tango-76, or Tango-83 which has an added amino-terminal methionine (useful for expression in prokaryotic cells).

The term "purified" as used herein refers to a nucleic acid or peptide that is substantially free of cellular material, viral material, or culture medium when produced by recombinant DNA techniques, or chemical precursors or other chemicals when chemically synthesized.

Polypeptides or other compounds of interest are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

The invention also features antibodies, e.g., monoclonal, polyclonal, and engineered antibodies, which specifically bind Tango-71, Tango-73, Tango-74, Tango-76, or Tango-83. An antibody which specifically binds to a given antigen is an antibody that recognizes and binds to a particular antigen, but which does not substantially recognize or bind to other molecules in a sample, e.g., a biological sample, which includes Tango-71, Tango-73, Tango-74, Tango-76, or Tango-83.

The invention also features antagonists and agonists of Tango-71, Tango-73, Tango-74, Tango-76, or Tango-83 that inhibit one or more of the biological activities of Tango-71, Tango-73, Tango-74, Tango-76, or Tango-83. Suitable antagonists can include small molecules (i.e., molecules with a molecular weight below about 500), large molecules (i.e., molecules with a molecular weight above about 500), neutralizing antibodies, polypeptides which compete with a native form of Tango-71, Tango-73, Tango-74, Tango-76, or Tango-83 for binding to a protein, and nucleic acid molecules that interfere with transcription of Tango-71, Tango-73, Tango-74, Tango-76, or Tango-83 (for example, antisense nucleic acid molecules and ribozymes). Agonists of Tango-71, Tango-73, Tango-74, Tango-76, and Tango-83 also include small and large molecules, and antibodies other than neutralizing antibodies.

The invention also features molecules which can increase or decrease the expression of Tango-71, Tango-73, Tango-74, Tango-76, or Tango-83 (e.g., by influencing transcription or translation). Small molecules (i.e., molecules with a molecular weight below about 500), large molecules (i.e., molecules with a molecular weight above about 500), and nucleic acid molecules that can be used to inhibit the expression of Tango-71, Tango-73, Tango-74, Tango-76, or Tango-83 (for example, antisense and ribozyme molecules) or to enhance their expression (for example, molecules that bind to a Tango-71, Tango-73, Tango-74, Tango-76, or Tango-83 transcription regulatory sequences and increase Tango-71, Tango-73, Tango-74, Tango-76, or Tango-83 transcription).

In addition, the invention features substantially pure polypeptides that functionally interact with Tango-71, Tango-73, Tango-74, Tango-76, or Tango-83, and the nucleic acid molecules that encode them.

The invention encompasses methods for treating disorders associated with aberrant expression or activity of a protein of the invention (i.e., Tango-71, Tango-73, Tango-74, Tango-76, or Tango-83). Thus, the invention includes methods for treating disorders associated with excessive expression or activity of a protein of the invention. Such methods entail administering a compound which decreases the expression or activity of the protein. The invention also includes methods for treating disorders associated with insufficient expression or activity of a protein of the invention. These methods entail administering a compound which increases the expression or activity of the protein.

The invention also features methods for detecting a protein of the invention (i.e., Tango-71, Tango-73, Tango-74, Tango-76, or Tango-83). Such methods include: obtaining a biological sample; contacting the sample with an antibody that specifically binds the protein under conditions which permit specific binding; and detecting any antibody-protein complexes formed.

In addition, the present invention encompasses methods and compositions for the diagnostic evaluation, typing, and prognosis of disorders associated with inappropriate expression or activity of a protein of the invention. For example, the nucleic acid molecules of the invention can be used as diagnostic hybridization probes to detect, for example, inappropriate expression of a protein of the invention or mutations in the gene encoding a protein of the invention gene. Such methods may be used to classify cells by the level of Tango-71, Tango-73, Tango-74, Tango-76, or Tango-83 expression.

The invention encompasses methods for diagnosing a disorder associated with aberrant activity of a protein of the invention, the methods including obtaining a biological sample from a patient and measuring the activity of the protein in the biological sample, wherein increased or decreased activity in the biological sample compared to a control indicates that the patient suffers from a disorder associated with aberrant activity of the protein.

The nucleic acid molecules of the invention can be used as primers for diagnostic PCR analysis for the identification of gene mutations, allelic variations and regulatory defects in the Tango-71, Tango-73, Tango-74, Tango-76, or Tango-83 gene. The present invention further provides for diagnostic kits for the practice of such methods.

The invention features methods of identifying compounds that modulate the expression or activity of a protein of the invention by assessing the expression or activity of the protein in the presence and absence of a selected compound. A difference in the level of expression or activity of the protein indicates that the selected compound is capable of modulating expression or activity of the protein. Expression can be assessed either at the level of gene expression (e.g., by measuring mRNA) or protein expression by techniques that are well known to skilled artisans. The activity of Tango-71, Tango-73, Tango-74, Tango-76, or Tango-83 can be assessed functionally.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description, and from the claims.

BRIEF DESCRIPTION OF THE DRAWINGS

FIGS. 1A–1E nucleotide sequence (SEQ ID NO:1) and deduced amino acid sequence (SEQ ID NO:2) of Tango-71.

FIGS. 2A–2B Nucleotide acid sequence (SEQ ID NO:3) and deduced amino acid sequence (SEQ ID NO:4) of Tango-73.

FIGS. 3A–3B Nucleotide acid sequence (SEQ ID NO:5) and deduced amino acid sequence (SEQ ID NO:6) of Tango-74. The ATG encoding the first Met is boxed as is the ATC encoding the final Ile.

FIG. 4 Nucleotide acid sequence of a 3' non-coding portion of Tango-74 (SEQ ID NO:11).

FIG. 5 Alignment of a portion of the amino acid sequence of Tango-74 (SEQ ID NO:6) and the amino acid sequence of TRAIL.

FIGS. 6A–6C Partial nucleotide sequence (SEQ ID NO:7) and deduced amino acid sequence (SEQ ID NO:8) of Tango-76.

FIG. 7 Nucleotide sequence of a 5' portion of Tango-83 (SEQ ID NO:9).

FIG. 8 Nucleotide sequence of a 3' portion of Tango-83 (SEQ ID NO:10).

FIGS. 9A–9B Alignment of amino acid sequence of Tango-71 and the amino acid sequence of ADAMTS-1.

FIG. 10 Alignment of the amino acid sequence of Tango-73 and the amino acid sequence of RVPI.

FIG. 11 Alignment of the amino acid sequence of Tango-73 and TMVCF.

FIG. 12 Alignment of amino acid sequence of Tango-76 and ADAMTS-1.

DETAILED DESCRIPTION

Tango-71, Tango-73, Tango-74, Tango-76, and Tango-83 Nucleic Acid Molecules

The Tango-71, Tango-73, Tango-74, Tango-76, and Tango-83 nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to sequences that only encode polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules of the invention encompass fragments that are not found as such in the natural state. Thus, the invention encompasses recombinant molecules, such as those in which a nucleic acid molecule (for example, an isolated nucleic acid molecule encoding Tango-71, Tango-73, Tango-74, Tango-76, or Tango-83) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

In the event the nucleic acid molecules of the invention encode or act as antisense molecules, they can be used for example, to regulate translation of Tango-71, Tango-73, Tango-74, Tango-76, or Tango-83 mRNA. Techniques associated with detection or regulation of Tango-71, Tango-73, Tango-74, Tango-76, or Tango-83 expression are well known to skilled artisans and can be used to diagnose and/or treat disorders associated with aberrant Tango-71, Tango-73, Tango-74, Tango-76, or Tango-83 expression.

The invention also encompasses nucleic acid molecules that hybridize under stringent conditions to a nucleic acid molecule encoding a Tango-71, Tango-73, Tango-74, Tango-76, or Tango-83 polypeptide (e.g., nucleic acid molecules having the sequence of the protein coding portion of SEQ ID NO:1, 3, 5, 7, or 9). The cDNA sequences described herein can be used to identify these hybridizing nucleic acids, which include, for example, nucleic acids that encode homologous polypeptides in other species and splice variants of the Tango-71, Tango-73, Tango-74, Tango-76, or Tango-83 gene in humans or other mammals. Accordingly, the invention features methods of detecting and isolating these nucleic acid molecules. Using these methods, a sample (for example, a nucleic acid library, such as a cDNA or genomic library) is contacted (or "screened") with a Tango-71, Tango-73, Tango-74, Tango-76, or Tango-83-specific probe (for example, a fragment of SEQ ID NO:1, 3, 5, 7, or 9 that is at least 25 or 50 or 100 nucleotides long). The probe will selectively hybridize to nucleic acids encoding related polypeptides (or to complementary sequences thereof). The probe, which can contain at least 25 (for example, 25, 50, 100, or 200 nucleotides) can be produced using any of several standard methods (see, for example, Ausubel et al.,"Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a Tango-71, Tango-73, Tango-74, Tango-76, or Tango-83-specific nucleic acid sequence that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2×SSC.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing Tango-71, Tango-73, Tango-74, Tango-76, and Tango-83-related coding sequences and/or their complements (that is, "antisense" sequence); (b) expression vectors that contain any of the foregoing Tango-71, Tango-73, Tango-74, Tango-76, and Tango-83-related coding sequences operatively associated with a regulatory element (examples of which are given below) that directs the expression of the coding sequences; (c) expression vectors containing, in addition to sequences encoding a Tango-71, Tango-73, Tango-74, Tango-76, or Tango-83 polypeptide, nucleic acid sequences that are unrelated to nucleic acid sequences encoding Tango-71, Tango-73, Tango-74, Tango-76, or Tango-83, such as molecules encoding a reporter or marker; and (d) genetically engineered host cells that contain any of the foregoing expression vectors and thereby express the nucleic acid molecules of the invention in the host cell.

Recombinant nucleic acid molecules can contain a sequence encoding a soluble Tango-71, Tango-73, Tango-74, Tango-76, or Tango-83 polypeptide; mature Tango-71, Tango-73, Tango-74, Tango-76, or Tango-83; or Tango-71, Tango-73, Tango-74, Tango-76, or Tango-83 having a signal sequence. A full length Tango-71, Tango-73, Tango-74, Tango-76, or Tango-83 polypeptide; a domain of Tango-71, Tango-73, Tango-74, Tango-76, or Tango-83; or a fragment thereof may be fused to additional polypeptides, as described below. Similarly, the nucleic acid molecules of the invention can encode the mature form of Tango-71, Tango-73, Tango-74, Tango-76, and Tango-83 or a form that encodes a polypeptide which facilitates secretion. In the latter instance, the polypeptide is typically referred to as a proprotein, which can be converted into an active form by removal of the signal sequence, for example, within the host cell. Proproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a Tango-71, Tango-73, Tango-74, Tango-76, or Tango-83 polypeptide and the second portion being, for example, the reporter described above or an immunoglobulin constant region.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding Tango-71, Tango-73, Tango-74, Tango-76, and Tango-83); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing Tango-71, Tango-73, Tango-74, Tango-76, or Tango-83 nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing Tango-71, Tango-73, Tango-74, Tango-76, or Tango-83 polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a Tango-71, Tango-73, Tango-74, Tango-76, or Tango-83 gene product in infected hosts (for example, see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines which stably express a Tango-71, Tango-73, Tango-74, Tango-76, or Tango-83 sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express Tango-71, Tango-73, Tango-74, Tango-76, or Tango-83. Such engineered cell lines may be particularly useful in screening and evaluation of compounds that affect the endogenous activity of the gene product.

A number of selection systems can be used. For example, the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in $tk^-$, $hgprt^-$ or $aprt^-$ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984).

Tango-71, Tango-73, Tango-74, Tango-76, and Tango-83 nucleic acid molecules are useful in genetic mapping and chromosome identification.

Tango-71, Tango-73, Tango-74, Tango-76, and Tango-83 Polypeptides

The Tango-71, Tango-73, Tango-74, Tango-76, and Tango-83 polypeptides described herein are those encoded by any of the nucleic acid molecules described above and include Tango-71, Tango-73, Tango-74, Tango-76, and Tango-83 fragments, mutants, truncated forms, and fusion proteins. These polypeptides can be prepared for a variety of uses, including but not limited to the generation of antibodies, as reagents in diagnostic assays, for the identification of other cellular gene products or compounds that can modulate the activity or expression of Tango-71, Tango-73, Tango-74, Tango-76, or Tango-83, and as pharmaceutical reagents useful for the treatment of disorders associated with aberrant expression or activity of Tango-71, Tango-73, Tango-74, Tango-76, or Tango-83.

Preferred polypeptides are substantially pure Tango-71, Tango-73, Tango-74, Tango-76, and Tango-83 polypeptides, including those that correspond to the polypeptide with an intact signal sequence, the secreted form of a Tango-71, Tango-73, Tango-74, Tango-76, or Tango-83 polypeptide. Especially preferred are polypeptides that are soluble under normal physiological conditions.

The invention also encompasses polypeptides that are functionally equivalent to Tango-71, Tango-73, Tango-74, Tango-76, and Tango-83. These polypeptides are equivalent to Tango-71, Tango-73, Tango-74, Tango-76, and Tango-83 in that they are capable of carrying out one or more of the functions of Tango-71, Tango-73, Tango-74, Tango-76, and Tango-83 in a biological system. Preferred Tango-71, Tango-73, Tango-74, Tango-76, and Tango-83 polypeptides have 20%, 40%, 50%, 75%, 80%, or even 90% of one or more of the biological activities of the full-length, mature human form of Tango-71, Tango-73, Tango-74, Tango-76, and Tango-83. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the summary of the invention.

Polypeptides that are functionally equivalent to Tango-71, Tango-73, Tango-74, Tango-76, or Tango-83 can be made using random mutagenesis techniques well known to those skilled in the art. It is more likely, however, that such polypeptides will be generated by site-directed mutagenesis (again using techniques well known to those skilled in the art). These polypeptides may have increased functionality or decreased functionality.

To design functionally equivalent polypeptides, it is useful to distinguish between conserved positions and variable positions. This can be done by aligning the amino acid sequence of Tango-71, Tango-73, Tango-74, Tango-76, or Tango-83 with the amino acid sequence of the homologons protein from another species. Skilled artisans will recognize that conserved amino acid residues are more likely to be necessary for preservation of function. Thus, it is preferable that conserved residues are not altered.

Mutations within the Tango-71, Tango-73, Tango-74, Tango-76, or Tango-83 coding sequence can be made to generate variant Tango-71, Tango-73, Tango-74, Tango-76, and Tango-83 genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur, and/or an amino acid deletion at the second position of any one or more of such recognition sequences, will prevent glycosylation at the modified tripeptide sequence (see, for example, Miyajima et al., *EMBO J.* 5:1193, 1986).

Alternatively, any fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$· nitriloacetic acid-agarose columns and histidine-tagged proteins are selectively eluted with imidazole-containing buffers.

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

The polypeptides of the invention can be chemically synthesized (for example, see Creighton, "Proteins: Structures and Molecular Principles," W. H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with Tango-71, Tango-73, Tango-74, Tango-76, or Tango-83 (and the genes that encode them) and thereby alter the function of Tango-71, Tango-73, Tango-74, Tango-76, or Tango-83. Interacting polypeptides can be identified using methods known to those skilled in the art. One suitable method is the "two-hybrid system," which detects protein interactions in vivo (Chien et al., *Proc. Natl. Acad. Sci. USA,* 88:9578, 1991). A kit for practicing this method is available from Clontech (Palo Alto, Calif.).

Transgenic Animals

Tango-71, Tango-73, Tango-74, Tango-76, and Tango-83 polypeptides can also be expressed in transgenic animals. These animals represent a model system for the study of disorders that are caused by or exacerbated by overexpression or underexpression of Tango-71, Tango-73, Tango-74, Tango-76, or Tango-83, and for the development of therapeutic agents that modulate the expression or activity of Tango-71, Tango-73, Tango-74, Tango-76, or Tango-83.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce a Tango-71, Tango-73, Tango-74, Tango-76, or Tango-83 transgene into animals to produce the founder lines of transgenic animals. Such techniques include, but are not limited to, pronuclear microinjection (U.S. Pat. No. 4,873, 191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry a the Tango-71, Tango-73, Tango-74, Tango-76, or Tango-83 transgene in all their cells, as well as animals that carry a transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the Tango-71, Tango-73, Tango-74, Tango-76, and Tango-83 transgene be integrated into the chromosomal site of the endogenous gene, gene targeting is preferred. Briefly, when such a technique is to be used, vectors containing some nucleotide sequences homologous to an endogenous Tango-71, Tango-73, Tango-74, Tango-76, or Tango-83 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous Tango-71, Tango-73, Tango-74, Tango-76, or Tango-83 gene in only that cell type (Gu et al., *Science* 265:103, 1984). The regulatory sequences required for such a cell-type specific inactivation will depend upon the particular cell type of interest, and will be apparent to those of skill in the art.

Once transgenic animals have been generated, expression of the recombinant Tango-71, Tango-73, Tango-74, Tango-76, or Tango-83 gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of Tango-71, Tango-73, Tango-74, Tango-76, or Tango-83 gene-expressing tissue can also be evaluated immunocytochemically using antibodies specific for the Tango-71, Tango-73, Tango-74, Tango-76, or Tango-83 transgene product.

For a review of techniques that can be used to generate and assess transgenic animals, skilled artisans can consult Gordon (*Intl. Rev. Cytol.* 115:171–229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science,* 244:1281, 1986; Wagner et al., U.S. Pat. No. 5,175,385; and Krimpenfort et al., U.S. Pat. No. 5,175,384 (the latter two publications are hereby incorporated by reference).

Anti-Tango-71, Tango-73, Tango-74, Tango-76, and Tango-83 Antibodies

Human Tango-71, Tango-73, Tango-74, Tango-76, and Tango-83 polypeptides (or immunogenic fragments or analogs) can be used to raise antibodies useful in the invention; such polypeptides can be produced by recombinant techniques or synthesized (see, for example, "Solid Phase Peptide Synthesis," supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a Tango-71, Tango-73, Tango-74, Tango-76, or Tango-83 protein or polypeptide. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the Tango-71, Tango-73, Tango-74, Tango-76, or Tango-83 polypeptides described above and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific Tango-71, Tango-73, Tango-74, Tango-76, or Tango-83 recognition by Western blot or immunoprecipitation analysis by standard methods, e.g., as described in Ausubel et al., supra. Antibodies that specifically recognize and bind to Tango-71, Tango-73, Tango-74, Tango-76, or Tango-83 are useful. For example, such antibodies can be used in an immunoassay to monitor the level of Tango-71, Tango-73, Tango-74, Tango-76, or Tango-83 produced by a mammal (for example, to determine the amount or subcellular location of Tango-71, Tango-73, Tango-74, Tango-76, or Tango-83).

Preferably, antibodies of the invention are produced using fragments of the Tango-71, Tango-73, Tango-74, Tango-76, or Tango-83 protein which lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera is also checked for its ability to immunoprecipitate recombinant Tango-71, Tango-73, Tango-74, Tango-76, or Tango-83 protein or control proteins, such as glucocorticoid receptor, CAT, or luciferase.

The antibodies can be used, for example, in the detection of the Tango-71, Tango-73, Tango-74, Tango-76, or Tango-83 in a biological sample as part of a diagnostic assay. Antibodies also can be used in a screening assay to measure the effect of a candidate compound on expression or localization of Tango-71, Tango-73, Tango-74, Tango-76, or Tango-83. Additionally, antibodies can be used in conjunction with the gene therapy techniques described to, for example, evaluate the normal and/or engineered Tango-71, Tango-73, Tango-74, Tango-76, or Tango-83-expressing cells prior to their introduction into the patient. Such antibodies additionally can be used in a method for inhibiting abnormal Tango-71, Tango-73, Tango-74, Tango-76, or Tango-83 activity.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a Tango-71, Tango-73, Tango-74, Tango-76, or Tango-83 polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to Tango-71, Tango-73, Tango-74, Tango-76, or Tango-83 can, in turn, be used to generate anti-idiotype antibodies that resemble a portion of Tango-71, Tango-73, Tango-74, Tango-76, or Tango-83 using techniques well known to those skilled in the art (see, e.g., Greenspan et al., *FASEB J.* 7:437, 1993; Nissinoff, *J. Immunol.* 147:2429, 1991). For example, antibodies that bind to Tango-71, Tango-73, Tango-74, Tango-76, or Tango-83 and competitively inhibit the binding of a binding partner of the protein can be used to generate anti-idiotypes that resemble a binding partner binding domain of the protein and, therefore, bind and neutralize a binding partner of the protein. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825, both of which are hereby incorporated by reference).

The methods described herein in which anti-Tango-71, Tango-73, Tango-74, Tango-76, or Tango-83 antibodies are employed may be performed, for example, by utilizing pre-packaged diagnostic kits comprising at least one specific Tango-71, Tango-73, Tango-74, Tango-76, or Tango-83 antibody reagent described herein, which may be conveniently used, for example, in clinical settings, to diagnose patients exhibiting symptoms of the disorders described below.

Antisense Nucleic Acids

Treatment regimes based on an "antisense" approach involve the design of oligonucleotides (either DNA or RNA) that are complementary to Tango-71, Tango-73, Tango-74, Tango-76, or Tango-83 mRNA. These oligonucleotides bind to the complementary Tango-71, Tango-73, Tango-74, Tango-76, or Tango-83 mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5' or 3' non-translated, non-coding regions of the mRNA, could be used in an antisense approach to inhibit translation of endogenous Tango-71, Tango-73, Tango-74, Tango-76, or Tango-83 mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-0-methylribonucleotide (Inoue et al., *Nucl. Acids Res.* 15:6131, 1987), or a chimeric RNA-DNA analog (Inoue et al., *FEBS Lett.* 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448, 1988).

The antisense molecules should be delivered to cells that express the protein of interest in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Tango-71, Tango-73, Tango-74, Tango-76, or Tango-83 transcripts and thereby prevent translation. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

Ribozymes

Ribozyme molecules designed to catalytically cleave Tango-71, Tango-73, Tango-74, Tango-76, or Tango-83 mRNA transcripts also can be used to prevent translation and expression of Tango-71, Tango-73, Tango-74, Tango-76, or Tango-83 (see, e.g., PCT Publication WO 90/11364; Saraver et al., *Science* 247:1222, 1990). While various ribozymes that cleave mRNA at site-specific recognition sequences can be used to destroy Tango-71, Tango-73, Tango-74, Tango-76, or Tango-83 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human Tango-71, Tango-73, Tango-74, Tango-76, and Tango-83 cDNA. Preferably, the ribozyme is engineered so that the cleavage recognition site is located near the 5' end of the mRNA, i.e., to increase efficiency and minimize the intracellular accumulation of non-functional mRNA transcripts.

The ribozymes of the present invention also include RNA endoribonucleases (hereinafter "Cech-type ribozymes") , such as the one that occurs naturally in Tetrahymena Thermophila (known as the IVS or L-19 IVS RNA), and which has been extensively described by Cech and his collaborators (Zaug et al., *Science* 224:574, 1984; Zaug et al., *Science*, 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in Tango-71, Tango-73, Tango-74, Tango-76, or Tango-83.

As in the antisense approach, the ribozymes can be composed of modified oligonucleotides (e.g., for improved stability, targeting, etc.), and should be delivered to cells which express Tango-71, Tango-73, Tango-74, Tango-76, or Tango-83 in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Other Methods for Reducing Tango-71, Tango-73, Tango-74, Tango-76, and Tango-83 Expression Endogenous Tango-71, Tango-73, Tango-74, Tango-76, and Tango-83 gene expression can also be reduced by inactivating the endogenous gene or its promoter using targeted homologous recombination (see, e.g., U.S. Pat. No. 5,464,764). For example, a mutant, non-functional Tango-71, Tango-73, Tango-74, Tango-76, or Tango-83 (or a completely unrelated DNA sequence) flanked by DNA homologous to the endogenous gene (either the coding regions or regulatory regions) can be used, with or without a selectable marker and/or a negative selectable marker, to transfect cells that express the endogenous gene in vivo. Insertion of the DNA construct, via targeted homologous recombination, results in inactivation of the Tango-71, Tango-73, Tango-74, Tango-76, or Tango-83 gene. Such approaches are particularly suited for use in the agricultural field where modifications to ES (embryonic stem) cells can be used to generate animal offspring with an inactive Tango-71, Tango-73, Tango-74, Tango-76, and Tango-83, However, this approach can be adapted for use in humans, provided the recombinant DNA constructs are directly administered or targeted to the required site in vivo using appropriate viral vectors.

Alternatively, endogenous Tango-71, Tango-73, Tango-74, Tango-76, or Tango-83 gene expression can be reduced by targeting deoxyribonucleotide sequences complementary to the regulatory region of the gene (i.e., the promoter and/or enhancers) to form triple helical structures that prevent transcription of the gene in target cells in the body (Helene *Anticancer Drug Res.* 6:569, 1981; Helene et al., *Ann. N.Y. Acad. Sci.* 660:27, 1992; and Maher, *Bioassays* 14:807, 1992).

Detecting Proteins Associated with Tango-71, Tango-73, Tango-74, Tango-76, or Tango-83

The invention also features polypeptides which interact with Tango-71, Tango-73, Tango-74, Tango-76, or Tango-83. Any method suitable for detecting protein-protein interactions may be employed for identifying transmembrane proteins, intracellular, or extracellular proteins that interact with Tango-71, Tango-73, Tango-74, Tango-76, or Tango-83. Among the traditional methods which may be employed are co-immunoprecipitation, crosslinking and co-purification through gradients or chromatographic columns of cell lysates or proteins obtained from cell lysates and the use of Tango-71, Tango-73, Tango-74, Tango-76, or Tango-83 to identify proteins in the lysate that interact with Tango-71, Tango-73, Tango-74, Tango-76, or Tango-83. For these assays, the Tango-71, Tango-73, Tango-74, Tango-76, or Tango-83 polypeptide can be: a full length Tango-71, Tango-73, Tango-74, Tango-76, or Tango-83; a soluble extracellular domain of Tango-71, Tango-73, Tango-74, Tango-76, or Tango-83; or some other suitable Tango-71, Tango-73, Tango-74, Tango-76, or Tango-83 polypeptide. Once isolated, such an interacting protein can be identified and cloned and then used, in conjunction with standard techniques, to identify proteins with which it interacts. For example, at least a portion of the amino acid sequence of a protein which interacts with the Tango-71, Tango-73, Tango-74, Tango-76, or Tango-83 can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known (Ausubel, supra; and "PCR Protocols: A Guide to Methods and Applications," Innis et al., eds. Academic Press, Inc., NY, 1990).

Additionally, methods may be employed which result directly in the identification of genes which encode proteins which interact with Tango-71, Tango-73, Tango-74, Tango-76, or Tango-83. These methods include, for example, screening expression libraries, in a manner similar to the well known technique of antibody probing of λgt11 libraries, using labeled Tango-71, Tango-73, Tango-74, Tango-76, or Tango-83 polypeptide or a Tango-71, Tango-73, Tango-74, Tango-76, and Tango-83 fusion protein, e.g., a Tango-71, Tango-73, Tango-74, Tango-76, and Tango-83 polypeptide or domain fused to a marker such as an enzyme, fluorescent dye, a luminescent protein, or to an IgFc domain.

There are also methods which are capable of detecting protein interaction. A method which detects protein interactions in vivo is the two-hybrid system (Chien et al., *Proc. Natl. Acad. Sci. USA*, 88:9578, 1991). A kit for practicing this method is available from Clontech (Palo Alto, Calif.).

Compounds which bind Tango-71, Tango-73, Tango-74, Tango-76, and Tango-83

Compounds which bind Tango-71, Tango-73, Tango-74, Tango-76, or Tango-83 can be identified using any standard binding assay. For example, candidate compounds can be bound to a solid support. Tango-71, Tango-73, Tango-74, Tango-76, or Tango-83 is then exposed to the immobilized compound and binding is measured (European Patent Application 84/03564).

EXAMPLES

Tango-71 cDNA (FIGS. 1A–1E; SEQ ID NO:1) was isolated from human melanocytes as follows.

Human melanocytes (Clonetics Corporation; San Diego, Calif.) were expanded in culture with Melanocyte Growth Media (MGM; Clonetics) according to the recommendations of the supplier. When the cells reached ~80–90% confluence, they were starved in MGM without growth factors for 46 hours. The starved cells were then stimulated with complete MGM supplemented with 20 ng/ml TNF (Gibco BRL; Gaithersburg, Md.) and cycloheximide (CHI;40 micrograms/ml) for 4 hours. Total RNA was isolated using the RNeasy Midi Kit (Qiagen; Chatsworth, Calif.), and the poly A+ fraction was further purified using Oligotex beads (Qiagen).

Three micrograms of poly A+ RNA were used to synthesize a cDNA library using the Superscript cDNA Synthesis kit (Gibco BRL). Complementary DNA was directionally cloned into the expression plasmid pMET7 using the SalI and NotI sites in the polylinker to construct a plasmid library. Transformants were picked and grown up for single-pass sequencing. Additionally, astrocyte cDNA was ligated into the SalI/NotI sites of the ZipLox vector (Gibco BRL) for construction of a lambda phage cDNA library.

Northern blot analysis of Tango-71 expression was performed using Tango-71 labeled with $^{32}$P-dCTP using the Prime-It kit (Stratagene, LaJolla, Calif.). Human mRNA blots (MTNI and MTNII; Clonetech; Palo Alto, Calif.) were probed and washed at high stringency as recommended by the manufacturer. Tango-71 is expressed as an approximately 6.0 kb transcript in all tissues: heart brain, placenta, lung, liver, skeletal muscle, kidney, pancreas, spleen, thymus, prostate, testes, ovary, small intestine, colon, PBLs.

The amino acid sequence of a portion of Tango-71 is 90% identical to the amino acid sequence of murine ADAMTS-1 (FIGS. 9A–9B), a cellular disintegrin and metalloprotease that is thought to be involved in inflammation and development of cancer cachexia (Kuno et al., *J. Biol. Chem.* 272:556, 1997). Based on sequence comparison to ADAMTS-1, Tango-71, using the amino acid numbering in FIGS. 9A–9B, has the following domains: amino acids 1–160 (metalloproteinase domain, partial); amino acids 170–242 (disintegrin domain); amino acids 257–307 (thrombospondin domain). A less apparent thrombospondin domain is present at amino acid 558–608. Portions of Tango-71 shown in FIGS. 1A–1E, but not in FIGS. 9A–9B, may also be homologous ADAMTS-1. Tango-71 may represent the human homolog of ADAMTS-1 or a splice variant thereof.

Tango-71 expression may be androgen regulated. Tango-71 expression in LNCaP cells, an androgen-dependent prostate cancer cell line, is induced by R1881, a testosterone analog. Tango-71 expression is downregulated in LNCaP cells treated with casodex, an anti-androgen.

Tango-73cDNA (FIGS. 2A–2B; SEQ ID NO:2) was isolated from human prostate epithelial cells as follows.

Human prostate epithelial cells (Clonetics) were expanded in culture with Prostate Epithelial Growth Medium (PEGM) (Clonetics). When cells reached confluence cells were grown in Prostate Basal Media (Clonetics) for 24 hours. They were stimulated with PEGM (prostate epithelial growth medium; Clonetics) and 40 ug/ml cycloheximide for 3 hours.

Total RNA was isolated using the RNeasy Midi Kit (Qiagen). Poly (A)+ was isolated using the Oligotex beads (Qiagen). Next, cDNA was constructed using the Superscript cDNA Synthesis Kit (Gibco BRL). The cDNA was cloned into the expression vector pMET7 using the SalI and NotI sites in the polylinker. Transformants were picked and sequenced.

Northern blot analysis of Tango-73expression was carried out as described above. This analysis revealed the presence of 4.0 kb and 3.0 kb transcripts in the placenta and liver. A 4.0 kb transcript was present in lung, kidney, thymus, prostate, spleen, testes, and colon, with the highest expression in lung, pancreas, prostate, and testes.

The amino acid sequence of Tango-73is 48% identical to rat RVP.1 (Briehl et al., *Mol. Endocrinol.* 5:1381, 1991) and 46.1% identical to TMVCF (Sirotkin et al., *Genomics* 42:245, 1997).

RVP.1 is up-regulated during apoptosis (Briehl et al., supra). TMVCF, a 219 amino acid protein with two putative membrane spanning domains, is deleted in velo-cardio-facial syndrome (Sirotkin et al., supra).

Tango-83 (FIGS. 7 and 8) and Tango-74 cDNAs (FIG. 5) were isolated from human astrocytes as follows.

Human astrocytes (Clonetics) were expanded in culture with Astocyte Growth Media (AGM; Clonetics) according to the recommendations of the supplier. When the cells reached ~80–90% confluence, they were stimulated with 200 units/ml Interleukin 1-Beta (Boehringer Mannheim) and cycloheximide (CHI: 40 micrograms/ml) for 4 hours. Total RNA was isolated using the RNeasy Midi Kit (Qiagen), and the poly A+ fraction was further purified using oligotex beads (Qiagen).

Three micrograms of poly A+ RNA were used to synthesize a cDNA library using the Superscript cDNA Synthesis kit (Gibco BRL). Complementary DNA was directionally cloned into the expression plasmid pMET7 using the SalI and NotI sites in the polylinker to construct a plasmid library. Transformants were picked and grown up for single-pass sequencing. Additionally, astrocyte cDNA was ligated into the SalI/NotI sites of the ZipLox vector (Gibco BRL) for construction of a lambda phage cDNA library.

Northern blot analysis of Tango-83 expression, performed as described above, revealed that Tango-83 is expressed as an approximately 9.0 kb transcript in brain (FIG. 13).

Northern blot analysis, performed as described above, revealed that Tango-74 is expressed as an approximately 4.0 kb transcript in heart, brain, lung, liver, kidney, pancreas, spleen, prostate, testes, ovary, small intestine, colon and peripheral blood lymphocytes. Higher expression was seen in lung, liver, skeletal muscle, spleen, testes, colon and peripheral blood lymphocytes.

The amino acid sequence of Tango-74 is homologous to the amino acid sequence of the TRAIL receptor (Pan et al., *Science* 276:111, 1997) (FIG. 5).

Tango-76 cDNA (SEQ ID NO:7) was isolated form an adult rat frontal cortex library. The amino acid sequence of Tango-76 is homologous to the amino acid sequence of ADAMTS-1 (FIG. 14).

Northern blot analysis of human mRNA probed with a Tango-76 probe revealed a 4.2 kb band in lung. Analysis of rat mRNA revealed a weak 3.8 kb transcript in heart, brain, spleen, liver, skeletal muscle, and kidney and a weak 1.8 kb transcript in spleen and liver.

Effective Dose

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

What is claimed is:

1. An isolated nucleic acid molecule comprising the nucleotide sequence of SEQ ID NO:1.

2. The nucleic acid molecule of claim 1, wherein the nucleic acid molecule consists of the nucleotide sequence of SEQ ID NO:1.

3. A vector comprising the nucleic acid molecule of claim 1.

4. The vector of claim 3 wherein the vector is an expression vector.

5. The nucleic acid molecule of claim 1 further comprising a nucleic acid sequence encoding a polypeptide that is not encoded by SEQ ID NO:1.

6. A host cell containing the nucleic acid molecule of any of claims 1, 3, 4, or 5.

7. The host cell of claim 6 which is a mammalian host cell.

8. A method for producing a polypeptide comprising culturing the host cell of claim 6 under conditions in which the nucleic acid molecule is expressed.

* * * * *

SEQUENCE LISTING

<160> NUMBER OF SEQ ID NOS: 16

<210> SEQ ID NO 1
<211> LENGTH: 4676
<212> TYPE: DNA
<213> ORGANISM: Homo sapiens
<220> FEATURE:
<221> NAME/KEY: CDS
<222> LOCATION: (460)...(3360)

<400> SEQUENCE: 1

```
gtcgacccac gcgtccgagc ggctccgagc caggggctat tgcaaagcca gggtgcgcta        60
ccggacggag aggggagagc cctgagcaga gtgagcaaca tcgcagccaa gcggaggcc        120 gaagagggc gccaggcacc aatctccgcg ttgcctcagc cccggaggcg ccccagagcg        180
cttcttgtcc cagcagagcc actctgcctg cgcctgcctc tcagtgtctc caactttgcg        240
ctggaagaaa aacttcccgc gcgccggcag aactgcagcg cctcctctta gtgactccgg        300
gagcttcggc tgtagccggc tctgcgcgcc cttccaacga ataatagaaa ttgttaattt        360
taacaatcca gagcaggcca acgaggcttt gctctcccga cccgaactaa agctccctcg        420
ctccgtgcgc tgctacgaac ggtgtctcct ggggctcca atg cag cga gct gtg         474
                                            Met Gln Arg Ala Val
                                              1               5 ccc gag ggg ttc gga agg cgc aag ctg ggc agc gac atg ggg aac gcg        522
Pro Glu Gly Phe Gly Arg Arg Lys Leu Gly Ser Asp Met Gly Asn Ala
             10                  15                  20 gag cgg gct ccg ggg tct cgg agc ttt ggg ccc gta ccc acg ctg ctg        570
Glu Arg Ala Pro Gly Ser Arg Ser Phe Gly Pro Val Pro Thr Leu Leu
         25                  30                  35 ctg ctc gcc gcg gcg cta ctg gcc gtg tcg gac gca ctc ggg cgc ccc        618
Leu Leu Ala Ala Ala Leu Leu Ala Val Ser Asp Ala Leu Gly Arg Pro
     40                  45                  50 tcc gag gag gac gag gag cta gtg gtg ccg gag ctg gag cgc gcc ccg        666
Ser Glu Glu Asp Glu Glu Leu Val Val Pro Glu Leu Glu Arg Ala Pro
 55                  60                  65 gga cac ggg acc acg cgc ctc cgc ctg cac gcc ttt gac cag cag ctg        714
Gly His Gly Thr Thr Arg Leu Arg Leu His Ala Phe Asp Gln Gln Leu
 70                  75                  80                  85 gat ctg gag ctg cgg ccc gac agc agc ttt ttg gcg ccc ggc ttc acg        762
Asp Leu Glu Leu Arg Pro Asp Ser Ser Phe Leu Ala Pro Gly Phe Thr
                 90                  95                 100 ctc cag aac gtg ggg cgc aaa tcc ggg tcc gag acg ccg ctt ccg gaa        810
Leu Gln Asn Val Gly Arg Lys Ser Gly Ser Glu Thr Pro Leu Pro Glu
            105                 110                 115 acc gac ctg gcg cac tgc ttc tac tcc ggc acc gtg aat ggc gat ccc        858
Thr Asp Leu Ala His Cys Phe Tyr Ser Gly Thr Val Asn Gly Asp Pro
        120                 125                 130 agc tcg gct gcc gcc ctc agc ctc tgc gag ggc gtg cgc ggc gcc ttc        906
Ser Ser Ala Ala Ala Leu Ser Leu Cys Glu Gly Val Arg Gly Ala Phe
    135                 140                 145
```

-continued

| | |
|---|---|
| tac ctg ctg ggg gag gcg tat ttc atc cag ccg ctg ccc gcc gcc agc<br>Tyr Leu Leu Gly Glu Ala Tyr Phe Ile Gln Pro Leu Pro Ala Ala Ser<br>150                       155                    160                    165 | 954 |
| gag cgc ctc gcc acc gcc gcc cca ggg gag aag ccg ccg gca cca cta<br>Glu Arg Leu Ala Thr Ala Ala Pro Gly Glu Lys Pro Pro Ala Pro Leu<br>                    170                    175                    180 | 1002 |
| cag ttc cac ctc ctg cgg cgg aat cgg cag ggc gac gta ggc ggc acg<br>Gln Phe His Leu Leu Arg Arg Asn Arg Gln Gly Asp Val Gly Gly Thr<br>                 185                    190                    195 | 1050 |
| tgc ggg gtc gtg gac gac gag ccc cgg ccg act ggg aaa gcg gag acc<br>Cys Gly Val Val Asp Asp Glu Pro Arg Pro Thr Gly Lys Ala Glu Thr<br>         200                    205                    210 | 1098 |
| gaa gac gag gac gaa ggg act gag ggc gag gac gaa ggg cct cag tgg<br>Glu Asp Glu Asp Glu Gly Thr Glu Gly Glu Asp Glu Gly Pro Gln Trp<br>215                       220                    225 | 1146 |
| tcg ccg cag gac ccg gca ctg caa ggc gta gga cag ccc aca gga act<br>Ser Pro Gln Asp Pro Ala Leu Gln Gly Val Gly Gln Pro Thr Gly Thr<br>230                       235                    240                    245 | 1194 |
| gga agc ata aga aag aag cga ttt gtg tcc agt cac cgc tat gtg gaa<br>Gly Ser Ile Arg Lys Lys Arg Phe Val Ser Ser His Arg Tyr Val Glu<br>                 250                    255                    260 | 1242 |
| acc atg ctt gtg gca gac cag tcg atg gca gaa ttc cac ggc agt ggt<br>Thr Met Leu Val Ala Asp Gln Ser Met Ala Glu Phe His Gly Ser Gly<br>         265                    270                    275 | 1290 |
| cta aag cat tac ctt ctc acg ttg ttt tcg gtg gca gcc aga ttg tac<br>Leu Lys His Tyr Leu Leu Thr Leu Phe Ser Val Ala Ala Arg Leu Tyr<br>280                       285                    290 | 1338 |
| aaa cac ccc agc att cgt aat tca gtt agc ctg gtg gtg gtg aag atc<br>Lys His Pro Ser Ile Arg Asn Ser Val Ser Leu Val Val Val Lys Ile<br>         295                    300                    305 | 1386 |
| ttg gtc atc cac gat gaa cag aag ggg ccg gaa gtg acc tcc aat gct<br>Leu Val Ile His Asp Glu Gln Lys Gly Pro Glu Val Thr Ser Asn Ala<br>310                       315                    320                    325 | 1434 |
| gcc ctc act ctg cgg aac ttt tgc aac tgg cag aag cag cac aac cca<br>Ala Leu Thr Leu Arg Asn Phe Cys Asn Trp Gln Lys Gln His Asn Pro<br>                 330                    335                    340 | 1482 |
| ccc agt gac cgg gat gca gag cac tat gac aca gca att ctt ttc acc<br>Pro Ser Asp Arg Asp Ala Glu His Tyr Asp Thr Ala Ile Leu Phe Thr<br>         345                    350                    355 | 1530 |
| aga cag gac ttg tgt ggg tcc cag aca tgt gat act ctt ggg atg gct<br>Arg Gln Asp Leu Cys Gly Ser Gln Thr Cys Asp Thr Leu Gly Met Ala<br>360                       365                    370 | 1578 |
| gat gtt gga act gtg tgt gat ccg agc aga agc tgc tcc gtc ata gaa<br>Asp Val Gly Thr Val Cys Asp Pro Ser Arg Ser Cys Ser Val Ile Glu<br>375                       380                    385 | 1626 |
| gat gat ggt tta caa gct gcc ttc acc aca gcc cat gaa tta ggc cac<br>Asp Asp Gly Leu Gln Ala Ala Phe Thr Thr Ala His Glu Leu Gly His<br>390                       395                    400                    405 | 1674 |
| gtg ttt aac atg cca cat gat gat gca aag cag tgt gcc agc ctt aat<br>Val Phe Asn Met Pro His Asp Asp Ala Lys Gln Cys Ala Ser Leu Asn<br>                 410                    415                    420 | 1722 |
| ggt gtg aac cag gat tcc cac atg atg gcg tca atg ctt tcc aac ctg<br>Gly Val Asn Gln Asp Ser His Met Met Ala Ser Met Leu Ser Asn Leu<br>         425                    430                    435 | 1770 |
| gac cac agc cag cct tgg tct cct tgc agt gcc tac atg att aca tca<br>Asp His Ser Gln Pro Trp Ser Pro Cys Ser Ala Tyr Met Ile Thr Ser<br>440                       445                    450 | 1818 |
| ttt ctg gat aat ggt cat ggg gaa tgt ttg atg gac aag cct cag aat<br>Phe Leu Asp Asn Gly His Gly Glu Cys Leu Met Asp Lys Pro Gln Asn<br>         455                    460                    465 | 1866 |

```
ccc ata cag ctc cca ggc gat ctc cct ggc acc tcg tac gat gcc aac    1914
Pro Ile Gln Leu Pro Gly Asp Leu Pro Gly Thr Ser Tyr Asp Ala Asn
470                 475                 480                 485 cgg cag tgc cag ttt aca ttt ggg gag gac tcc aaa cac tgc ccc gat    1962
Arg Gln Cys Gln Phe Thr Phe Gly Glu Asp Ser Lys His Cys Pro Asp
            490                 495                 500 gca gcc agc aca tgt agc acc ttg tgg tgt acc ggc acc tct ggt ggg    2010
Ala Ala Ser Thr Cys Ser Thr Leu Trp Cys Thr Gly Thr Ser Gly Gly
        505                 510                 515 gtg ctg gtg tgt caa acc aaa cac ttc ccg tgg gcg gat ggc acc agc    2058
Val Leu Val Cys Gln Thr Lys His Phe Pro Trp Ala Asp Gly Thr Ser
    520                 525                 530 tgt gga gaa ggg aaa tgg tgt atc aac ggc aag tgt gtg aac aaa acc    2106
Cys Gly Glu Gly Lys Trp Cys Ile Asn Gly Lys Cys Val Asn Lys Thr
535                 540                 545 gac aga aag cat ttt gat acg cct ttt cat gga agc tgg gga atg tgg    2154
Asp Arg Lys His Phe Asp Thr Pro Phe His Gly Ser Trp Gly Met Trp
550                 555                 560                 565 ggg cct tgg gga gac tgt tcg aga acg tgc ggt gga gga gtc cag tac    2202
Gly Pro Trp Gly Asp Cys Ser Arg Thr Cys Gly Gly Gly Val Gln Tyr
            570                 575                 580 acg atg agg gaa tgt gac aac cca gtc cca aag aat gga ggg aag tac    2250
Thr Met Arg Glu Cys Asp Asn Pro Val Pro Lys Asn Gly Gly Lys Tyr
        585                 590                 595 tgt gaa ggc aaa cga gtg cgc tac aga tcc tgt aac ctt gag gac tgt    2298
Cys Glu Gly Lys Arg Val Arg Tyr Arg Ser Cys Asn Leu Glu Asp Cys
    600                 605                 610 cca gac aat aat gga aaa acc ttt aga gag gaa caa tgt gaa gca cac    2346
Pro Asp Asn Asn Gly Lys Thr Phe Arg Glu Glu Gln Cys Glu Ala His
615                 620                 625 aac gag ttt tca aaa gct tcc ttt ggg agt ggg cct gcg gtg gaa tgg    2394
Asn Glu Phe Ser Lys Ala Ser Phe Gly Ser Gly Pro Ala Val Glu Trp
630                 635                 640                 645 att ccc aag tac gct ggc gtc tca cca aag gac agg tgc aag ctc atc    2442
Ile Pro Lys Tyr Ala Gly Val Ser Pro Lys Asp Arg Cys Lys Leu Ile
            650                 655                 660 tgc caa gcc aaa ggc att ggc tac ttc ttc gtt ttg cag ccc aag gtt    2490
Cys Gln Ala Lys Gly Ile Gly Tyr Phe Phe Val Leu Gln Pro Lys Val
        665                 670                 675 gta gat ggt act cca tgt agc cca gat tcc acc tct gtc tgt gtg caa    2538
Val Asp Gly Thr Pro Cys Ser Pro Asp Ser Thr Ser Val Cys Val Gln
    680                 685                 690 gga cag tgt gta aaa gct ggt tgt gat cgc atc ata gac tcc aaa aag    2586
Gly Gln Cys Val Lys Ala Gly Cys Asp Arg Ile Ile Asp Ser Lys Lys
695                 700                 705 aag ttt gat aaa tgt ggt gtt tgc ggg gga aat gga tct act tgt aaa    2634
Lys Phe Asp Lys Cys Gly Val Cys Gly Gly Asn Gly Ser Thr Cys Lys
710                 715                 720                 725 aaa ata tca gga tca gtt act agt gca aaa cct gga tat cat gat atc    2682
Lys Ile Ser Gly Ser Val Thr Ser Ala Lys Pro Gly Tyr His Asp Ile
            730                 735                 740 atc aca att cca act gga gcc acc aac atc gaa gtg aaa cag cgg aac    2730
Ile Thr Ile Pro Thr Gly Ala Thr Asn Ile Glu Val Lys Gln Arg Asn
        745                 750                 755 cag agg gga tcc agg aac aat ggc agc ttt ctt gcc atc aaa gct gct    2778
Gln Arg Gly Ser Arg Asn Asn Gly Ser Phe Leu Ala Ile Lys Ala Ala
    760                 765                 770 gat ggc aca tat att ctt aat ggt gac tac act ttg tcc acc tta gag    2826
Asp Gly Thr Tyr Ile Leu Asn Gly Asp Tyr Thr Leu Ser Thr Leu Glu
775                 780                 785
```

```
caa gac att atg tac aaa ggt gtt gtc ttg agg tac agc ggc tcc tct    2874
Gln Asp Ile Met Tyr Lys Gly Val Val Leu Arg Tyr Ser Gly Ser Ser
790             795                 800                 805 gcg gca ttg gaa aga att cgc agc ttt agc cct ctc aaa gag ccc ttg    2922
Ala Ala Leu Glu Arg Ile Arg Ser Phe Ser Pro Leu Lys Glu Pro Leu
                810                 815                 820 acc atc cag gtt ctt act gtg ggc aat gcc ctt cga cct aaa att aaa    2970
Thr Ile Gln Val Leu Thr Val Gly Asn Ala Leu Arg Pro Lys Ile Lys
                825                 830                 835 tac acc tac ttc gta aag aag aag aag gaa tct ttc aat gct atc ccc    3018
Tyr Thr Tyr Phe Val Lys Lys Lys Lys Glu Ser Phe Asn Ala Ile Pro
            840                 845                 850 act ttt tca gca tgg gtc att gaa gag tgg ggc gaa tgt tct aag tca    3066
Thr Phe Ser Ala Trp Val Ile Glu Glu Trp Gly Glu Cys Ser Lys Ser
        855                 860                 865 tgt gaa ttg ggt tgg cag aga aga ctg gta gaa tgc cga gac att aat    3114
Cys Glu Leu Gly Trp Gln Arg Arg Leu Val Glu Cys Arg Asp Ile Asn
870                 875                 880                 885 gga cag cct gct tcc gag tgt gca aag gaa gtg aag cca gcc agc acc    3162
Gly Gln Pro Ala Ser Glu Cys Ala Lys Glu Val Lys Pro Ala Ser Thr
                890                 895                 900 aga cct tgt gca gac cat ccc tgc ccc cag tgg cag ctg ggg gag tgg    3210
Arg Pro Cys Ala Asp His Pro Cys Pro Gln Trp Gln Leu Gly Glu Trp
                905                 910                 915 tca tca tgt tct aag acc tgt ggg aag ggt tac aaa aaa aga agc ttg    3258
Ser Ser Cys Ser Lys Thr Cys Gly Lys Gly Tyr Lys Lys Arg Ser Leu
            920                 925                 930 aag tgt ctg tcc cat gat gga ggg gtg tta tct cat gag agc tgt gat    3306
Lys Cys Leu Ser His Asp Gly Gly Val Leu Ser His Glu Ser Cys Asp
935                 940                 945 cct tta aag aaa cct aaa cat ttc ata gac ttt tgc aca atg gca gaa    3354
Pro Leu Lys Lys Pro Lys His Phe Ile Asp Phe Cys Thr Met Ala Glu
950                 955                 960                 965 tgc agt taagtggttt aagtggtgtt agctttgagg gcaaggcaaa gtgaggaagg     3410
Cys Ser gctggtgcag ggaaagcaag aaggctggag ggatccagcg tatcttgcca gtaaccagtg  3470
aggtgtatca gtaaggtggg attatggggg tagatagaaa aggagttgaa tcatcagagt  3530
aaactgccag ttgcaaattt gataggatag ttagtgagga ttattaacct ctgagcagtg  3590
atatagcata ataaagcccc gggcattatt attattattt cttttgttac atctattaca  3650
agtttagaaa aaacaaagca attgtcaaaa aaagttagaa ctattacaac ccctgtttcc  3710
tggtacttat caaatactta gtatcatggg ggttgggaaa tgaaaagtag gagaaaagtg  3770
agattttact aagacctgtt ttactttacc tcactaacaa tgggggagaa aaggagtaca  3830
aataggatct tgaccagca ctgtttatgg ctgctgtggt ttcagagaat gtttatacat   3890
tatttctacc gagaattaaa acttcagatt gttcaacatg agaaaaggc tcagcaacgt   3950 gaaataacgc aaatggcttc ctctttcctt ttttggacca tctcagtctt tatttgtgta  4010
attcattttg aggaaaaaac aactccatgt atttattcaa gtgcattaaa gtctacaatg  4070 gaaaaaagc agtgaagcat tacatgctgg taaaagctag aggagacaca atgagcttag   4130
tacctccaac ttcctttctt tcctaccatg taaccctgct ttcggaatat ggatgtaaag  4190
aagtaacttg tgtctcatga aaatcagtac aatcacacaa ggaggatgaa acgccggaac  4250
aaaaatgagg tgtgtagaac aggtcccac aggtttgggg acattgagat cacttgtctt   4310
gtggtgggga ggctgctgag gggtagcagg tccatctcca gcagctggtc caacagtcgt  4370
```

-continued

```
atcctggtga atgtctgttc agctcttctg tgagaatatg atttttttcca tatgtatata    4430 gtaaaatatg ttactataaa ttacatgtac tttataagta ttggtttggg tgttccttcc    4490
aagaaggact atagttagta ataaatgcct ataataacat atttattttt atacatttat    4550
ttctaatgaa aaaacttttt aaattatatc gcttttgtgg aagtgcatat aaaatagagt    4610
atttatacaa tatatgttac tagaaataaa agaacacttt tggaaaaaaa aaaaaaaaaa    4670
aaaaaa                                                                4676
```

<210> SEQ ID NO 2
<211> LENGTH: 967
<212> TYPE: PRT
<213> ORGANISM: Homo sapiens

<400> SEQUENCE: 2

```
Met Gln Arg Ala Val Pro Glu Gly Phe Gly Arg Arg Lys Leu Gly Ser
  1               5                  10                  15

Asp Met Gly Asn Ala Glu Arg Ala Pro Gly Ser Arg Ser Phe Gly Pro
             20                  25                  30

Val Pro Thr Leu Leu Leu Ala Ala Ala Leu Leu Ala Val Ser Asp
         35                  40                  45

Ala Leu Gly Arg Pro Ser Glu Glu Asp Glu Glu Leu Val Val Pro Glu
     50                  55                  60

Leu Glu Arg Ala Pro Gly His Gly Thr Thr Arg Leu Arg Leu His Ala
 65                  70                  75                  80

Phe Asp Gln Gln Leu Asp Leu Glu Leu Arg Pro Asp Ser Ser Phe Leu
                 85                  90                  95

Ala Pro Gly Phe Thr Leu Gln Asn Val Gly Arg Lys Ser Gly Ser Glu
            100                 105                 110

Thr Pro Leu Pro Glu Thr Asp Leu Ala His Cys Phe Tyr Ser Gly Thr
        115                 120                 125

Val Asn Gly Asp Pro Ser Ser Ala Ala Ala Leu Ser Leu Cys Glu Gly
    130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
            180                 185                 190

Asp Val Gly Gly Thr Cys Gly Val Val Asp Asp Glu Pro Arg Pro Thr
        195                 200                 205

Gly Lys Ala Glu Thr Glu Asp Glu Asp Glu Gly Thr Glu Gly Glu Asp
    210                 215                 220

Glu Gly Pro Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
                245                 250                 255

His Arg Tyr Val Glu Thr Met Leu Val Ala Asp Gln Ser Met Ala Glu
            260                 265                 270

Phe His Gly Ser Gly Leu Lys His Tyr Leu Leu Thr Leu Phe Ser Val
        275                 280                 285

Ala Ala Arg Leu Tyr Lys His Pro Ser Ile Arg Asn Ser Val Ser Leu
    290                 295                 300

Val Val Val Lys Ile Leu Val Ile His Asp Glu Gln Lys Gly Pro Glu
305                 310                 315                 320
```

-continued

```
Val Thr Ser Asn Ala Ala Leu Thr Leu Arg Asn Phe Cys Asn Trp Gln
            325                 330                 335

Lys Gln His Asn Pro Ser Asp Arg Asp Ala Glu His Tyr Asp Thr
            340                 345                 350

Ala Ile Leu Phe Thr Arg Gln Asp Leu Cys Gly Ser Gln Thr Cys Asp
            355                 360                 365

Thr Leu Gly Met Ala Asp Val Gly Thr Val Cys Asp Pro Ser Arg Ser
    370                 375                 380

Cys Ser Val Ile Glu Asp Gly Leu Gln Ala Ala Phe Thr Thr Ala
385                 390                 395                 400

His Glu Leu Gly His Val Phe Asn Met Pro His Asp Asp Ala Lys Gln
                405                 410                 415

Cys Ala Ser Leu Asn Gly Val Asn Gln Asp Ser His Met Met Ala Ser
            420                 425                 430

Met Leu Ser Asn Leu Asp His Ser Gln Pro Trp Ser Pro Cys Ser Ala
            435                 440                 445

Tyr Met Ile Thr Ser Phe Leu Asp Asn Gly His Gly Glu Cys Leu Met
    450                 455                 460

Asp Lys Pro Gln Asn Pro Ile Gln Leu Pro Gly Asp Leu Pro Gly Thr
465                 470                 475                 480

Ser Tyr Asp Ala Asn Arg Gln Cys Gln Phe Thr Phe Gly Glu Asp Ser
                485                 490                 495

Lys His Cys Pro Asp Ala Ala Ser Thr Cys Ser Thr Leu Trp Cys Thr
            500                 505                 510

Gly Thr Ser Gly Gly Val Leu Val Cys Gln Thr Lys His Phe Pro Trp
    515                 520                 525

Ala Asp Gly Thr Ser Cys Gly Glu Gly Lys Trp Cys Ile Asn Gly Lys
    530                 535                 540

Cys Val Asn Lys Thr Asp Arg Lys His Phe Asp Thr Pro Phe His Gly
545                 550                 555                 560

Ser Trp Gly Met Trp Gly Pro Trp Gly Asp Cys Ser Arg Thr Cys Gly
                565                 570                 575

Gly Gly Val Gln Tyr Thr Met Arg Glu Cys Asp Asn Pro Val Pro Lys
                580                 585                 590

Asn Gly Gly Lys Tyr Cys Glu Gly Lys Arg Val Arg Tyr Arg Ser Cys
            595                 600                 605

Asn Leu Glu Asp Cys Pro Asp Asn Asn Gly Lys Thr Phe Arg Glu Glu
            610                 615                 620

Gln Cys Glu Ala His Asn Glu Phe Ser Lys Ala Ser Phe Gly Ser Gly
625                 630                 635                 640

Pro Ala Val Glu Trp Ile Pro Lys Tyr Ala Gly Val Ser Pro Lys Asp
                645                 650                 655

Arg Cys Lys Leu Ile Cys Gln Ala Lys Gly Ile Gly Tyr Phe Phe Val
            660                 665                 670

Leu Gln Pro Lys Val Val Asp Gly Thr Pro Cys Ser Pro Asp Ser Thr
            675                 680                 685

Ser Val Cys Val Gln Gly Gln Cys Val Lys Ala Gly Cys Asp Arg Ile
            690                 695                 700

Ile Asp Ser Lys Lys Lys Phe Asp Lys Cys Gly Val Cys Gly Gly Asn
705                 710                 715                 720

Gly Ser Thr Cys Lys Lys Ile Ser Gly Ser Val Thr Ser Ala Lys Pro
            725                 730                 735
```

-continued

```
Gly Tyr His Asp Ile Ile Thr Ile Pro Thr Gly Ala Thr Asn Ile Glu
            740                 745                 750
Val Lys Gln Arg Asn Gln Arg Gly Ser Arg Asn Asn Gly Ser Phe Leu
            755                 760                 765
Ala Ile Lys Ala Ala Asp Gly Thr Tyr Ile Leu Asn Gly Asp Tyr Thr
            770                 775                 780
Leu Ser Thr Leu Glu Gln Asp Ile Met Tyr Lys Gly Val Val Leu Arg
785                 790                 795                 800
Tyr Ser Gly Ser Ala Ala Leu Glu Arg Ile Arg Ser Phe Ser Pro
                    805                 810                 815
Leu Lys Glu Pro Leu Thr Ile Gln Val Leu Thr Val Gly Asn Ala Leu
            820                 825                 830
Arg Pro Lys Ile Lys Tyr Thr Tyr Phe Val Lys Lys Lys Glu Ser
            835                 840                 845
Phe Asn Ala Ile Pro Thr Phe Ser Ala Trp Val Ile Glu Glu Trp Gly
            850                 855                 860
Glu Cys Ser Lys Ser Cys Glu Leu Gly Trp Gln Arg Arg Leu Val Glu
865                 870                 875                 880
Cys Arg Asp Ile Asn Gly Gln Pro Ala Ser Glu Cys Ala Lys Glu Val
                    885                 890                 895
Lys Pro Ala Ser Thr Arg Pro Cys Ala Asp His Pro Cys Pro Gln Trp
            900                 905                 910
Gln Leu Gly Glu Trp Ser Ser Cys Ser Lys Thr Cys Gly Lys Gly Tyr
            915                 920                 925
Lys Lys Arg Ser Leu Lys Cys Leu Ser His Asp Gly Gly Val Leu Ser
            930                 935                 940
His Glu Ser Cys Asp Pro Leu Lys Lys Pro Lys His Phe Ile Asp Phe
945                 950                 955                 960
Cys Thr Met Ala Glu Cys Ser
                965

<210> SEQ ID NO 3
<211> LENGTH: 3483
<212> TYPE: DNA
<213> ORGANISM: Homo sapiens
<220> FEATURE:
<221> NAME/KEY: CDS
<222> LOCATION: (240)...(872)

<400> SEQUENCE: 3
gtcgacccac gcgtccgggg agcaaccgca gcttctagta tccagactcc agcgccgccc      60
cgggcgcgga ccccaacccc gacccagagc ttctccagcg gcggcgcagc gagcagggct     120
ccccgcctta acttcctccg cggggcccag ccaccttcgg gagtccgggt tgcccacctg     180
caaactctcc gccttctgca cctgccaccc ctgagccagc gcgggcgccc gagcgagtc      239 atg gcc aac gcg ggg ctg cag ctg ttg ggc ttc att ctc gcc ttc ctg       287
Met Ala Asn Ala Gly Leu Gln Leu Leu Gly Phe Ile Leu Ala Phe Leu
 1               5                  10                  15 gga tgg atc ggc gcc atc gtc agc act gcc ctg ccc cag tgg agg att       335
Gly Trp Ile Gly Ala Ile Val Ser Thr Ala Leu Pro Gln Trp Arg Ile
                20                  25                  30 tac tcc tat gcc ggc gac aac atc gtg acc gcc cag gcc atg tac gag       383
Tyr Ser Tyr Ala Gly Asp Asn Ile Val Thr Ala Gln Ala Met Tyr Glu
            35                  40                  45 ggg ctg tgg atg tcc tgc gtg tcg cag agc acc ggg cag atc cag tgc       431
Gly Leu Trp Met Ser Cys Val Ser Gln Ser Thr Gly Gln Ile Gln Cys
        50                  55                  60
```

-continued

| | |
|---|---|
| aaa gtc ttt gac tcc ttg ctg aat ctg agc agc aca ttg caa gca acc<br>Lys Val Phe Asp Ser Leu Leu Asn Leu Ser Ser Thr Leu Gln Ala Thr<br>65                        70                     75                   80 | 479 |
| cgt gcc ttg atg gtg gtt ggc atc ctc ctg gga gtg ata gca atc ttt<br>Arg Ala Leu Met Val Val Gly Ile Leu Leu Gly Val Ile Ala Ile Phe<br>                     85                     90                   95 | 527 |
| gtg gcc acc gtt ggc atg aag tgt atg aag tgc ttg gaa gac gat gag<br>Val Ala Thr Val Gly Met Lys Cys Met Lys Cys Leu Glu Asp Asp Glu<br>100                     105                   110 | 575 |
| gtg cag aag atg agg atg gct gtc att ggg ggt gcg ata ttt ctt ctt<br>Val Gln Lys Met Arg Met Ala Val Ile Gly Gly Ala Ile Phe Leu Leu<br>        115                   120                   125 | 623 |
| gca ggt ctg gct att tta gtt gcc aca gca tgg tat ggc aat aga atc<br>Ala Gly Leu Ala Ile Leu Val Ala Thr Ala Trp Tyr Gly Asn Arg Ile<br>130                     135                   140 | 671 |
| gtt caa gaa ttc tat gac cct atg acc cca gtc aat gcc agg tac gaa<br>Val Gln Glu Phe Tyr Asp Pro Met Thr Pro Val Asn Ala Arg Tyr Glu<br>145                     150                   155                   160 | 719 |
| ttt ggt cag gct ctc ttc act ggc tgg gct gct gct tct ctc tgc ctt<br>Phe Gly Gln Ala Leu Phe Thr Gly Trp Ala Ala Ala Ser Leu Cys Leu<br>                     165                   170                   175 | 767 |
| ctg gga ggt gcc cta ctt tgc tgt tcc tgt ccc cga aaa aca acc tct<br>Leu Gly Gly Ala Leu Leu Cys Cys Ser Cys Pro Arg Lys Thr Thr Ser<br>180                     185                   190 | 815 |
| tac cca aca cca agg ccc tat cca aaa cct gca cct tcc agc ggg aaa<br>Tyr Pro Thr Pro Arg Pro Tyr Pro Lys Pro Ala Pro Ser Ser Gly Lys<br>        195                   200                   205 | 863 |
| gac tac gtg tgacacagag gcaaaggag aaaatcatgt tgaaacaaac<br>Asp Tyr Val<br>   210 | 912 |
| cgaaaatgga cattgagata ctatcattaa cattaggacc ttagaatttt gggtattgta | 972 |
| atctgaagta tggtattaca aaacaaacaa acaaacaaaa aacccatgtg ttaaaatact | 1032 |
| cagtgctaaa catggcttaa tcttatttta tcttctttcc tcaatatagg agggaagatt | 1092 |
| tttccatttg tattactgct tcccattgag taatcatact caactggggg aagggtgct | 1152 |
| ccttaaatat atatagatat gtatatatac atgttttcct attaaaaata gacagtaaaa | 1212 |
| tactattctc attatgttga tactagcata cttaaaatat ctctaaaata ggtaaatgta | 1272 |
| tttaattcca tattgatgaa gatgtttatt ggtatatttt ctttttcgtc tatatataca | 1332 |
| tatgtaacag tcaaatatca tttactcttc tcattagct ttgggtgcct ttgccacaag | 1392 |
| acctagccta atttaccaag gatgaattct ttcaattctt catgcgtgcc ttttcatat | 1452 |
| acttatttta ttttttacca taatcttata gcacttgcat cgttattaag ccctatttg | 1512 |
| ttttgtgttt cattggtctc tatctcctga atctaacaca tttcatagcc tacatttag | 1572 |
| tttctaaagc caagaagaat ttattacaaa tcagaacttt ggaggcaaat ctttctgcat | 1632 |
| gaccaaagtg ataaattcct gttgaccttc ccacacaatc cctgtactct gacccatagc | 1692 |
| actcttgttt gctttgaaaa tatttgtcca attgagtagc tgcatgctgt tcccccaggt | 1752 |
| gttgtaacac aactttattg attgaatttt taagctactt attcatagtt ttatatcccc | 1812 |
| ctaaactacc tttttgttcc ccattcctta attgtattgt tttcccaagt gtaattatca | 1872 |
| tgcgttttat atcttcctaa taaggtgtgg tctgtttgtc tgaacaaagt gctagacttt | 1932 |
| ctggagtgat aatctggtga caaatattct ctctgtagct gtaagcaagt cacttaatct | 1992 |
| ttctacctct ttttctatc tgccaaattg agataatgat acttaaccag ttagaagagg | 2052 |
| tagtgtgaat attaattagt ttatattact ctcattcttt gaacatgaac tatgcctatg | 2112 |

-continued

```
tagtgtcttt atttgctcag ctggctgaga cactgaagaa gtcactgaac aaaacctaca    2172
cacgtacctt catgtgattc actgccttcc tctctctacc agtctatttc cactgaacaa    2232
aacctacaca cataccttca tgtggttcag tgccttcctc tctctaccag tctatttcca    2292
ctgaacaaaa cctacgcaca taccttcatg tggctcagtg ccttcctctc tctaccagtc    2352
tatttccatt ctttcagctg tgtctgacat gtttgtgctc tgttccattt taacaactgc    2412
tcttactttt ccagtctgta cagaatgcta tttcacttga gcaagatgat gtaatggaaa    2472
gggtgttggc attggtgtct ggagacctgg atttgagtct tggtgctatc aatcaccgtc    2532
tgtgtttgag caaggcattt ggctgctgta agcttattgc ttcatctgta agcggtggtt    2592
tgtaattcct gatcttccca cctcacagtg atgttgtggg gatccagtga gatagaatac    2652
atgtaagtgt ggttttgtaa tttaaaaagt gctatactaa gggaaagaat tgaggaatta    2712
actgcatacg ttttggtgtt gcttttcaaa tgtttgaaaa caaaaaaaat gttaagaaat    2772
gggtttcttg ccttaaccag tctctcaagt gatgagacag tgaagtaaaa ttgagtgcac    2832
taaacaaata agattctgag gaagtcttat cttctgcagt gagtatggcc cgatgctttc    2892
tgtggctaaa cagatgtaat gggaagaaat aaaagcctac gtgttggtaa atccaacagc    2952
aagggagatt tttgaatcat aataactcat aaggtgctat ctgttcagtg atgccctcag    3012
agctcttgct gttagctggc agctgacgct gctaggatag ttagtttgga aatggtactt    3072
cataataaac tacacaagga aagtcagcca ctgtgtctta tgaggaattg gacctaataa    3132
attttagtgt gccttccaaa cctgagaata tatgcttttg gaagttaaaa tttaaatggc    3192
ttttgccaca tacatagatc ttcatgatgt gtgagtgtaa ttccatgtgg atatcagtta    3252
ccaaacatta caaaaaaatt ttatggccca aaatgaccaa cgaaattgtt acaatagaat    3312
ttatccaatt tgatctttt tatattcttc taccacacct ggaaacagac caatagacat    3372 tttggggtttt tataatagga atttgtataa agcattactc tttttcaata aattgttttt    3432
taatttaaaa aaaggaaaaa aaaaaaaaaa aaaaaaaaaa agggcggccg c              3483
```

<210> SEQ ID NO 4
<211> LENGTH: 211
<212> TYPE: PRT
<213> ORGANISM: Homo sapiens

<400> SEQUENCE: 4

```
Met Ala Asn Ala Gly Leu Gln Leu Leu Gly Phe Ile Leu Ala Phe Leu
 1               5                  10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125
```

-continued

```
Ala Gly Leu Ala Ile Leu Val Ala Thr Ala Trp Tyr Gly Asn Arg Ile
    130                 135                 140
Val Gln Glu Phe Tyr Asp Pro Met Thr Pro Val Asn Ala Arg Tyr Glu
145                 150                 155                 160
Phe Gly Gln Ala Leu Phe Thr Gly Trp Ala Ala Ser Leu Cys Leu
                165                 170                 175
Leu Gly Gly Ala Leu Leu Cys Cys Ser Cys Pro Arg Lys Thr Thr Ser
            180                 185                 190
Tyr Pro Thr Pro Arg Pro Tyr Pro Lys Pro Ala Pro Ser Ser Gly Lys
        195                 200                 205
Asp Tyr Val
    210
```

<210> SEQ ID NO 5
<211> LENGTH: 3569
<212> TYPE: DNA
<213> ORGANISM: Homo sapiens
<220> FEATURE:
<221> NAME/KEY: CDS
<222> LOCATION: (104)...(1261)

<400> SEQUENCE: 5

| | | |
|---|---|---|
| gtcgacccac gcgtccggct gcgagaacct ttgcacgcgc acaaactacg gggacgattt | 60 |
| ctgattgatt tttggcgctt tcgatccacc ctcctccctt ctc atg gga ctt tgg | 115 |
|                                                  Met Gly Leu Trp |
|                                                    1              |

```
gga caa agc gtc ccg acc gcc tcg agc gct cga gca ggg cgc tat cca    163
Gly Gln Ser Val Pro Thr Ala Ser Ser Ala Arg Ala Gly Arg Tyr Pro
  5                  10                  15                  20 gga gcc agg aca gcg tcg gga acc aga cca tgg ctc ctg gac tcc aag    211
Gly Ala Arg Thr Ala Ser Gly Thr Arg Pro Trp Leu Leu Asp Ser Lys
                 25                  30                  35 atc ctt aag ttc gtc gtc ttc atc gtc gcg gtt ctg ctg ccg gtc cgg    259
Ile Leu Lys Phe Val Val Phe Ile Val Ala Val Leu Leu Pro Val Arg
             40                  45                  50 gtt gac tct gcc acc atc ccc cgg cag gac gaa gtt ccc cag cag aca    307
Val Asp Ser Ala Thr Ile Pro Arg Gln Asp Glu Val Pro Gln Gln Thr
         55                  60                  65 gtg gcc cca cag caa cag agg cgc agc ctc aag gag gag gag tgt cca    355
Val Ala Pro Gln Gln Gln Arg Arg Ser Leu Lys Glu Glu Glu Cys Pro
 70                  75                  80 gca gga tct cat aga tca gaa tat act gga gcc tgt aac ccg tgc aca    403
Ala Gly Ser His Arg Ser Glu Tyr Thr Gly Ala Cys Asn Pro Cys Thr
 85                  90                  95                 100 gag ggt gtg gat tac acc att gct tcc aac aat ttg cct tct tgc ctg    451
Glu Gly Val Asp Tyr Thr Ile Ala Ser Asn Asn Leu Pro Ser Cys Leu
                105                 110                 115 cta tgt aca gtt tgt aaa tca ggt caa aca aat aaa agt tcc tgt acc    499
Leu Cys Thr Val Cys Lys Ser Gly Gln Thr Asn Lys Ser Ser Cys Thr
            120                 125                 130 acg acc aga gac acc gtg tgt cag tgt gaa aaa gga agc ttc cag gat    547
Thr Thr Arg Asp Thr Val Cys Gln Cys Glu Lys Gly Ser Phe Gln Asp
        135                 140                 145 aaa aac tcc cct gag atg tgc cgg acg tgt aga aca ggg tgt ccc aga    595
Lys Asn Ser Pro Glu Met Cys Arg Thr Cys Arg Thr Gly Cys Pro Arg
    150                 155                 160 ggg atg gtc aag gtc agt aat tgt acg ccc cgg agt gac atc aag tgc    643
Gly Met Val Lys Val Ser Asn Cys Thr Pro Arg Ser Asp Ile Lys Cys
165                 170                 175                 180
```

```
aaa aat gaa tca gct gcc agt tcc act ggg aaa acc cca gca gcg gag      691
Lys Asn Glu Ser Ala Ala Ser Ser Thr Gly Lys Thr Pro Ala Ala Glu
                185                 190                 195 gag aca gtg acc acc atc ctg ggg atg ctt gcc tct ccc tat cac tac      739
Glu Thr Val Thr Thr Ile Leu Gly Met Leu Ala Ser Pro Tyr His Tyr
        200                 205                 210 ctt atc atc ata gtg gtt tta gtc atc att tta gct gtg gtt gtg gtt      787
Leu Ile Ile Ile Val Val Leu Val Ile Ile Leu Ala Val Val Val Val
            215                 220                 225 ggc ttt tca tgt cgg aag aaa ttc att tct tac ctc aaa ggc atc tgc      835
Gly Phe Ser Cys Arg Lys Lys Phe Ile Ser Tyr Leu Lys Gly Ile Cys
230                 235                 240 tca ggt ggt gga gga ggt ccc gaa cgt gtg cac aga gtc ctt ttc cgg      883
Ser Gly Gly Gly Gly Gly Pro Glu Arg Val His Arg Val Leu Phe Arg
245                 250                 255                 260 cgg cgt tca tgt cct tca cga gtt cct ggg gcg gag gac aat gcc cgc      931
Arg Arg Ser Cys Pro Ser Arg Val Pro Gly Ala Glu Asp Asn Ala Arg
                265                 270                 275 aac gag acc ctg agt aac aga tac ttg cag ccc acc cag gtc tct gag      979
Asn Glu Thr Leu Ser Asn Arg Tyr Leu Gln Pro Thr Gln Val Ser Glu
        280                 285                 290 cag gaa atc caa ggt cag gag ctg gca gag cta aca ggt gtg act gta     1027
Gln Glu Ile Gln Gly Gln Glu Leu Ala Glu Leu Thr Gly Val Thr Val
            295                 300                 305 gag tcg cca gag gag cca cag cgt ctg ctg gaa cag gca gaa gct gaa     1075
Glu Ser Pro Glu Glu Pro Gln Arg Leu Leu Glu Gln Ala Glu Ala Glu
310                 315                 320 ggg tgt cag agg agg agg ctg ctg gtt cca gtg aat gac gct gac tcc     1123
Gly Cys Gln Arg Arg Arg Leu Leu Val Pro Val Asn Asp Ala Asp Ser
325                 330                 335                 340 gct gac atc agc acc ttg ctg gat gcc tcg gca aca ctg gaa gaa gga     1171
Ala Asp Ile Ser Thr Leu Leu Asp Ala Ser Ala Thr Leu Glu Glu Gly
                345                 350                 355 cat gca aag gaa aca att cag gac caa ctg gtg ggc tcc gaa aag ctc     1219
His Ala Lys Glu Thr Ile Gln Asp Gln Leu Val Gly Ser Glu Lys Leu
        360                 365                 370 ttt tat gaa gaa gat gaa gca ggc tct gct acg tcc tgc ctg             1261
Phe Tyr Glu Glu Asp Glu Ala Gly Ser Ala Thr Ser Cys Leu
            375                 380                 385 tgaaagaatc tcttcaggaa accagagctt ccctcattta ccttttctcc tacaaaggga   1321
agcagcctgg aagaaacagt ccagtacttg acccatgccc caacaaactc tactatccaa   1381 tatgggcag cttaccaatg gtcctagaac tttgttaacg cacttggagt aattttatg     1441 aaatactgcg tgtgataagc aaacgggaga aatttatatc agattcttgg ctgcatagtt   1501
atacgattgt gtattaaggg tcgttttagg ccacatgcgg tggctcatgc ctgtaatccc   1561
agcactttga taggctgagg caggtggatt gcttgagctc gggagtttga gaccagcctc   1621
atcaacacag tgaaactcca tctcaattta aaaagaaaaa aagtggtttt aggatgtcat   1681
tctttgcagt tcttcatcat gagacaagtc ttttttttctg cttcttatat tgcaagctcc  1741
atctctactg gtgtgtgcat ttaatgacat ctaactacag atgccgcaca gccacaatgc   1801
tttgccttat aatttttttaa ctttagaacg ggattatctt gttattacct gtattttcag  1861
tttcggatat ttttgactta atgatgagat tatcaagacg tagccctatg ctaagtcatg   1921
agcatatgga cttacgaggg ttcgacttag agttttgagc tttaagatac gattattggg   1981
gcttaccccc accttaatta gagaaacatt tatattgctt actactgtag gctgtacatc   2041
tcttttccga tttttgtata atgatgtaaa catggaaaaa ctttaggaaa tgcacttatt   2101
```

-continued

```
aggctgttta catgggttgc ctggatacaa atcagcagtc aaaaatgact aaaaatataa    2161
ctagtgacgg agggagaaat cctccctctg tgggaggcac ttactgcatt ccagttctcc    2221
ctcctgcgcc ctgagactgg accagggttt gatggctggc agcttctcaa ggggcagctt    2281
gtcttacttg ttaattttag aggtatatag ccatatttat ttataaataa atatttattt    2341
atttatttat aagtagatgt ttacatatgc ccaggatttt gaagagcctg gtatctttgg    2401
gaagccatgt gtctggtttg tcgtgctggg acagtcatgg gactgcatct tccgacttgt    2461
ccacagcaga tgaggacagt gagaattaag ttagatccga gactgcgaag agcttctctt    2521
tcaagcgcca ttacagttga acgttagtga atcttgagcc tcatttgggc tcagggcaga    2581
gcaggtgttt atctgccccg gcatctgcca tggcatcaag agggaagagt ggacggtgct    2641
tgggaatggt gtgaaatggt tgccgactca ggcatggatg ggcccctctc gcttctggtg    2701
gtctgtgaac tgagtccctg ggatgccttt tagggcagag attcctgagc tgcgttttag    2761
ggtacagatt ccctgtttga ggagcttggc ccctctgtaa gcatctgact catctcagag    2821
atatcaattc ttaaacactg tgacaacagg atctaaaatg gctgacacat ttgtccttgt    2881
gtcacgttcc attattttat ttaaaaacct cagtaatcgt tttagcttct ttccagcaaa    2941
ctcttctcca cagtagccca gtcgtggtag gataaattac ggatatagtc attctagggg    3001
tttcagtctt ttccatctca aggcattgtg tgttttgttc cggactggt  ttggctggga    3061 caaagttaga actgcctgaa gttcgcacat tcagattgtt gtgtccatgg agttttagga    3121
ggggatggcc tttccggtct tcgcacttcc atcctctccc acttccatct ggcgtcccac    3181
accttgtccc ctgcacttct ggatgacaca gggtgctgct gcctcctagt ctttgccttt    3241
gctgggcctt ctgtgcagga gacttggtct caaagctcag agagagccag tccggtccca    3301
gctcctttgt cccttcctca gaggccttcc ttgaagatgc atctagacta ccagccttat    3361
cagtgtttaa gcttattcct ttaacataag cttcctgaca acatgaaatt gttggggttt    3421
tttggcgttg gttgaattgt ttaggttttg ctttataccc gggccaaata gcacataaca    3481
cctggttata tatgaaatac tcatatgttt atgaccaaaa taaatatgaa acctcatatt    3541
aaaaaaaaaa aaaaaaaagg gcggccgc                                      3569
```

<210> SEQ ID NO 6
<211> LENGTH: 386
<212> TYPE: PRT
<213> ORGANISM: Homo sapiens

<400> SEQUENCE: 6

```
Met Gly Leu Trp Gly Gln Ser Val Pro Thr Ala Ser Ser Ala Arg Ala
 1               5                  10                  15

Gly Arg Tyr Pro Gly Ala Arg Thr Ala Ser Gly Thr Arg Pro Trp Leu
            20                  25                  30

Leu Asp Ser Lys Ile Leu Lys Phe Val Phe Ile Val Ala Val Leu
        35                  40                  45

Leu Pro Val Arg Val Asp Ser Ala Thr Ile Pro Arg Gln Asp Glu Val
    50                  55                  60

Pro Gln Gln Thr Val Ala Pro Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110
```

```
Pro Ser Cys Leu Leu Cys Thr Val Cys Lys Ser Gly Gln Thr Asn Lys
        115                 120                 125

Ser Ser Cys Thr Thr Thr Arg Asp Thr Val Cys Gln Cys Glu Lys Gly
    130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
            180                 185                 190

Pro Ala Ala Glu Glu Thr Val Thr Thr Ile Leu Gly Met Leu Ala Ser
        195                 200                 205

Pro Tyr His Tyr Leu Ile Ile Ile Val Val Leu Val Ile Ile Leu Ala
210                 215                 220

Val Val Val Gly Phe Ser Cys Arg Lys Lys Phe Ile Ser Tyr Leu
225                 230                 235                 240

Lys Gly Ile Cys Ser Gly Gly Gly Gly Pro Glu Arg Val His Arg
                245                 250                 255

Val Leu Phe Arg Arg Arg Ser Cys Pro Ser Arg Val Pro Gly Ala Glu
                260                 265                 270

Asp Asn Ala Arg Asn Glu Thr Leu Ser Asn Arg Tyr Leu Gln Pro Thr
            275                 280                 285

Gln Val Ser Glu Gln Glu Ile Gln Gly Gln Glu Leu Ala Glu Leu Thr
    290                 295                 300

Gly Val Thr Val Glu Ser Pro Glu Glu Pro Gln Arg Leu Leu Glu Gln
305                 310                 315                 320

Ala Glu Ala Glu Gly Cys Gln Arg Arg Arg Leu Leu Val Pro Val Asn
                325                 330                 335

Asp Ala Asp Ser Ala Asp Ile Ser Thr Leu Leu Asp Ala Ser Ala Thr
            340                 345                 350

Leu Glu Glu Gly His Ala Lys Glu Thr Ile Gln Asp Gln Leu Val Gly
        355                 360                 365

Ser Glu Lys Leu Phe Tyr Glu Glu Asp Glu Ala Gly Ser Ala Thr Ser
370                 375                 380

Cys Leu
385

<210> SEQ ID NO 7
<211> LENGTH: 2114
<212> TYPE: DNA
<213> ORGANISM: Rattus rattus
<220> FEATURE:
<221> NAME/KEY: CDS
<222> LOCATION: (3)...(1445)

<400> SEQUENCE: 7 gc gtc cgg aac aag acg ctg ccc tgg tct ccc tgc agt gct gtc tac    47
   Val Arg Asn Lys Thr Leu Pro Trp Ser Pro Cys Ser Ala Val Tyr
   1               5                   10                  15 ctc acg gag ctc ctg gat gat ggt cac gga gac tgc ctc ctg gat gat    95
Leu Thr Glu Leu Leu Asp Asp Gly His Gly Asp Cys Leu Leu Asp Asp
            20                  25                  30 ggc cac agc acc ctc tat gag ctg gac cag cag tgc aag cag atc ttt   143
Gly His Ser Thr Leu Tyr Glu Leu Asp Gln Gln Cys Lys Gln Ile Phe
        35                  40                  45
```

```
ggg cct gat ttc cga cac tgc ccc aac acc tct gtg gag gac atc tgt         191
Gly Pro Asp Phe Arg His Cys Pro Asn Thr Ser Val Glu Asp Ile Cys
        50                  55                  60 gtc cag ctc tgg tgc cgt cat cgg gat agt gat gag ccc att tgc cac         239
Val Gln Leu Trp Cys Arg His Arg Asp Ser Asp Glu Pro Ile Cys His
    65                  70                  75 aca aag aat gcc agc ttg ctc tgg gct gat ggt acg ccc tgt ggc cct         287
Thr Lys Asn Ala Ser Leu Leu Trp Ala Asp Gly Thr Pro Cys Gly Pro
80                  85                  90                  95 ggg cac ctg tgc ctg gat ggt agc tgt gtg ctc cgg gag gaa gta gag         335
Gly His Leu Cys Leu Asp Gly Ser Cys Val Leu Arg Glu Glu Val Glu
                100                 105                 110 aat ccc aag gct gtg gta gat gga gac tgg ggt ccc tgg gga ccc tgg         383
Asn Pro Lys Ala Val Val Asp Gly Asp Trp Gly Pro Trp Gly Pro Trp
            115                 120                 125 gga caa tgt tct cgc acc tgt ggt gga ggg ata cag ttt tcg aac cgt         431
Gly Gln Cys Ser Arg Thr Cys Gly Gly Gly Ile Gln Phe Ser Asn Arg
        130                 135                 140 gag tgt gat aat cca gca cct cag aat gga gga aga ttt tgc ctg gga         479
Glu Cys Asp Asn Pro Ala Pro Gln Asn Gly Gly Arg Phe Cys Leu Gly
    145                 150                 155 gag aga gtc aag tac caa tct tgc aag aca gag gaa tgt cca cca aat         527
Glu Arg Val Lys Tyr Gln Ser Cys Lys Thr Glu Glu Cys Pro Pro Asn
160                 165                 170                 175 gga aaa agc ttc agg gag cag cag tgt gaa aaa tat aat gcc tac aac         575
Gly Lys Ser Phe Arg Glu Gln Gln Cys Glu Lys Tyr Asn Ala Tyr Asn
                180                 185                 190 cac acg gac ctg gat ggg aat ttc ctt cag tgg gtc ccc aaa tac tca         623
His Thr Asp Leu Asp Gly Asn Phe Leu Gln Trp Val Pro Lys Tyr Ser
            195                 200                 205 gga gtg tcc ccc cga gac cga tgc aaa ctg ttt tgc aga gcc cgt ggg         671
Gly Val Ser Pro Arg Asp Arg Cys Lys Leu Phe Cys Arg Ala Arg Gly
        210                 215                 220 agg agt gag ttc aaa gtg ttt gaa act aag gtg atc gat ggc act ctg         719
Arg Ser Glu Phe Lys Val Phe Glu Thr Lys Val Ile Asp Gly Thr Leu
    225                 230                 235 tgc gga ccg gat act ctg gcc atc tgt gtg cgg gga cag tgc gtt aag         767
Cys Gly Pro Asp Thr Leu Ala Ile Cys Val Arg Gly Gln Cys Val Lys
240                 245                 250                 255 gct ggc tgt gac cat gtg gtg aac tca cct aag aag ctg gac aag tgt         815
Ala Gly Cys Asp His Val Val Asn Ser Pro Lys Lys Leu Asp Lys Cys
                260                 265                 270 ggg gtg tgt ggg ggc aaa ggc act gcc tgt agg aag gtc tca ggt tct         863
Gly Val Cys Gly Gly Lys Gly Thr Ala Cys Arg Lys Val Ser Gly Ser
            275                 280                 285 ttc acc ccc ttc agt tat ggc tac aat gac att gtc acc atc cca gct         911
Phe Thr Pro Phe Ser Tyr Gly Tyr Asn Asp Ile Val Thr Ile Pro Ala
        290                 295                 300 ggt gcc aca aat att gat gtg aaa caa cgg agc cac cca ggg gtc cag         959
Gly Ala Thr Asn Ile Asp Val Lys Gln Arg Ser His Pro Gly Val Gln
    305                 310                 315 aat gac ggc agc tac ctg gca ctg aag aca gcc aat ggg cag tac ctg        1007
Asn Asp Gly Ser Tyr Leu Ala Leu Lys Thr Ala Asn Gly Gln Tyr Leu
320                 325                 330                 335 ctc aat ggt aac cta gcc atc tct gcc ata gag caa gac atc ttg atg        1055
Leu Asn Gly Asn Leu Ala Ile Ser Ala Ile Glu Gln Asp Ile Leu Met
                340                 345                 350 aag ggg acc atc cta aag tac agt ggt tcc atg gcc acc ctg gag cgg        1103
Lys Gly Thr Ile Leu Lys Tyr Ser Gly Ser Met Ala Thr Leu Glu Arg
            355                 360                 365
```

-continued

```
ctg cag agc ttc caa gcc ctc cct gag cct ctt aca gta cag ctc ctg   1151
Leu Gln Ser Phe Gln Ala Leu Pro Glu Pro Leu Thr Val Gln Leu Leu
        370                 375                 380 act gtg tct ggt gag gtc ttc cct cca aaa gtc aaa tat acc ttc ttc   1199
Thr Val Ser Gly Glu Val Phe Pro Pro Lys Val Lys Tyr Thr Phe Phe
385                 390                 395 gtc ccc aat gac acg gac ttc aac gtg cag agt agc aaa gaa aga gca   1247
Val Pro Asn Asp Thr Asp Phe Asn Val Gln Ser Ser Lys Glu Arg Ala
400                 405                 410                 415 agc acc aac atc att cag tcc ttg ccc tat gca gag tgg gtg ctg ggg   1295
Ser Thr Asn Ile Ile Gln Ser Leu Pro Tyr Ala Glu Trp Val Leu Gly
                420                 425                 430 gac tgg tct gaa tgt cca agc aca tgt gga ggt ggc tgg cag cgg cgg   1343
Asp Trp Ser Glu Cys Pro Ser Thr Cys Gly Gly Gly Trp Gln Arg Arg
            435                 440                 445 act gtg gaa tgc agg gac ccc tca ggt cag gcc tct gac acc tgt gat   1391
Thr Val Glu Cys Arg Asp Pro Ser Gly Gln Ala Ser Asp Thr Cys Asp
        450                 455                 460 gag gct ctg aaa cct gag gat gcc aag ccc tgt gga agc cag cca tgt   1439
Glu Ala Leu Lys Pro Glu Asp Ala Lys Pro Cys Gly Ser Gln Pro Cys
465                 470                 475 ctc ctc tgatcccctt ggtggacatg tctaaggctt atggatttgg gctactggcg   1495
Leu Leu
480 tacagacaaa ggtctcctct gaggtgacac tacatatcaa gatggcatgg cccttccagg   1555 ccttctatta ctcaaccct ttgggtacca cctaattcat aaggaagaga gaagaggat    1615 taagggtaac agactgtaaa gttgactgtc tagtggactg gaccttgttt atgaccaaga   1675 agatgggata ggttaaaagg taaaagtgtg cttattgatc caaggtgag atttcagaac   1735 cagcctcttt gcaaaggact agaaaggtta aatgagaaag aagatttttt ttctctttg   1795 gtttctccaa taatcaatct acctcacagc gggaggaact tggtgtataa ggccaggtgt   1855 tagtggtgag tgccaaggca ctctccatag atatcttcga gccatcttca gaaatggcca   1915 tggctgtttt cagtattaaa actctgttgt ctcaaaaggt ggtggtgtcc atcacagggt   1975 tatagaaagc cacttgttct caggctgcct cctgctgggg cggacccctt tcaagtattt   2035 atgcaaatat gtttctgaac taaagtgtga tcttacacca aaaaaaaaaa aaaaaaaaa    2095 aaaaaaaaaa ggcggccgc                                                2114
```

```
<210> SEQ ID NO 8
<211> LENGTH: 481
<212> TYPE: PRT
<213> ORGANISM: Rattus rattus

<400> SEQUENCE: 8

Val Arg Asn Lys Thr Leu Pro Trp Ser Pro Cys Ser Ala Val Tyr Leu
1               5                   10                  15

Thr Glu Leu Leu Asp Asp Gly His Gly Asp Cys Leu Leu Asp Asp Gly
                20                  25                  30

His Ser Thr Leu Tyr Glu Leu Asp Gln Gln Cys Lys Gln Ile Phe Gly
            35                  40                  45

Pro Asp Phe Arg His Cys Pro Asn Thr Ser Val Glu Asp Ile Cys Val
        50                  55                  60

Gln Leu Trp Cys Arg His Arg Asp Ser Asp Glu Pro Ile Cys His Thr
65                  70                  75                  80

Lys Asn Ala Ser Leu Leu Trp Ala Asp Gly Thr Pro Cys Gly Pro Gly
                85                  90                  95
```

-continued

```
His Leu Cys Leu Asp Gly Ser Cys Val Leu Arg Glu Val Glu Asn
            100                 105                 110
Pro Lys Ala Val Val Asp Gly Asp Trp Gly Pro Trp Gly Pro Trp Gly
        115                 120                 125
Gln Cys Ser Arg Thr Cys Gly Gly Ile Gln Phe Ser Asn Arg Glu
    130                 135                 140
Cys Asp Asn Pro Ala Pro Gln Asn Gly Gly Arg Phe Cys Leu Gly Glu
145                 150                 155                 160
Arg Val Lys Tyr Gln Ser Cys Lys Thr Glu Glu Cys Pro Asn Gly
                165                 170                 175
Lys Ser Phe Arg Glu Gln Gln Cys Glu Lys Tyr Asn Ala Tyr Asn His
                180                 185                 190
Thr Asp Leu Asp Gly Asn Phe Leu Gln Trp Val Pro Lys Tyr Ser Gly
            195                 200                 205
Val Ser Pro Arg Asp Arg Cys Lys Leu Phe Cys Arg Ala Arg Gly Arg
        210                 215                 220
Ser Glu Phe Lys Val Phe Glu Thr Lys Val Ile Asp Gly Thr Leu Cys
225                 230                 235                 240
Gly Pro Asp Thr Leu Ala Ile Cys Val Arg Gly Gln Cys Val Lys Ala
                245                 250                 255
Gly Cys Asp His Val Val Asn Ser Pro Lys Lys Leu Asp Lys Cys Gly
                260                 265                 270
Val Cys Gly Gly Lys Gly Thr Ala Cys Arg Lys Val Ser Gly Ser Phe
        275                 280                 285
Thr Pro Phe Ser Tyr Gly Tyr Asn Asp Ile Val Thr Ile Pro Ala Gly
    290                 295                 300
Ala Thr Asn Ile Asp Val Lys Gln Arg Ser His Pro Gly Val Gln Asn
305                 310                 315                 320
Asp Gly Ser Tyr Leu Ala Leu Lys Thr Ala Asn Gly Gln Tyr Leu Leu
                325                 330                 335
Asn Gly Asn Leu Ala Ile Ser Ala Ile Glu Gln Asp Ile Leu Met Lys
            340                 345                 350
Gly Thr Ile Leu Lys Tyr Ser Gly Ser Met Ala Thr Leu Glu Arg Leu
        355                 360                 365
Gln Ser Phe Gln Ala Leu Pro Glu Pro Leu Thr Val Gln Leu Leu Thr
    370                 375                 380
Val Ser Gly Glu Val Phe Pro Pro Lys Val Lys Tyr Thr Phe Phe Val
385                 390                 395                 400
Pro Asn Asp Thr Asp Phe Asn Val Gln Ser Ser Lys Glu Arg Ala Ser
                405                 410                 415
Thr Asn Ile Ile Gln Ser Leu Pro Tyr Ala Glu Trp Val Leu Gly Asp
            420                 425                 430
Trp Ser Glu Cys Pro Ser Thr Cys Gly Gly Gly Trp Gln Arg Arg Thr
        435                 440                 445
Val Glu Cys Arg Asp Pro Ser Gly Gln Ala Ser Asp Thr Cys Asp Glu
    450                 455                 460
Ala Leu Lys Pro Glu Asp Ala Lys Pro Cys Gly Ser Gln Pro Cys Leu
465                 470                 475                 480
Leu
```

<210> SEQ ID NO 9
<211> LENGTH: 1448
<212> TYPE: DNA
<213> ORGANISM: Homo sapiens

<400> SEQUENCE: 9

```
gtcgacccac gcgtccgggg aagcttgcc agcagatctg cagctgccaa aatggggcag      60
actgtgacag tgtgactgga aagtgcacct gtgccccagg attcaaagga attgactgct    120
ctaccccatg ccctctggga acctatggga taaactgttc ctctcgctgt ggctgtaaaa    180
atgatgcagt ctgctctcct gtggacgggt cttgtacttg caaggcaggc tggcacgggg    240
tggactgctc catcagatgt cccagtggca catgggcctt tggctgtaac ttaacatgcc    300
agtgcctcaa cggggagcc tgcaacaccc tggacgggac ctgcacgtgt gcacctggat     360
ggcgcgggga gaaatgcgaa cttccctgcc aggatggcac gtacgggctg aactgtgctg    420
agcgctgcga ctgcagccac gcagatggct gccaccctac cacgggccat tgccgctgcc    480
tccccggatg gtcaggtgtc cactgtgaca gcgtgtgtgc tgagggacgc tggggcccca    540
actgctccct gccctgctac tgtaaaaatg gggcttcatg ctcccctgat gatggcatct    600
gcgagtgtgc accaggcttc cgaggcacca cttgtcagag gatctgctcc cctggttttt    660
atgggcatcg ctgcagccag acatgcccac agtgcgttca cagcagcggg ccctgccacc    720
acatcaccgg cctgtgtgac tgcttgcctg gcttcacagg cgccctctgc aatgaagtgt    780
gtcccagtgg cagatttggg aaaaactgtg caggaatttg tacctgcacc aacaacggaa    840
cctgtaaccc cattgacaga tcttgtcagt gttaccccgg ttggattggc agtgactgct    900
ctcaaccatg tccacctgcc cactggggcc caaactgcat ccacacgtgc aactgccata    960
atggagcttt ctgcagcgcc tacgatgggg aatgtaaatg cactcctggc tggacagggc   1020
tctactgcac tcagagatgt cctctagggt tttatggaaa agattgtgca ctgatatgcc   1080
aatgtcaaaa cggagctgac tgcgaccaca tttctgggca gtgtacttgc cgcactggat   1140
tcatgggacg gcactgtgag cagaagtgcc cttcaggaac atatggctat ggctgtcgcc   1200
agatatgtga ttgtctgaac aactccacct gcgaccacat cactgggacc tgttactgca   1260
gccccggatg gaagggagcg agatgtgatc aagctggtgt tatcatagtt ggaaatctga   1320
acagcttaag ccgaaccagt actgctctcc ctgctgattc ctaccaaatc ggggccattg   1380
caggcatcat cattcttgtc ctagttgttc tcttcctact ggcattgttc attatttata   1440
gacacagc                                                             1448
```

<210> SEQ ID NO 10
<211> LENGTH: 1578
<212> TYPE: DNA
<213> ORGANISM: Homo sapiens
<220> FEATURE:
<221> NAME/KEY: misc_feature
<222> LOCATION: (1)...(1578)
<223> OTHER INFORMATION: n = A,T,C or G

<400> SEQUENCE: 10

```
nagcccaaca ggaatgttct atgaaagtga acctaacagt gagtgttgtt cccaaggagt      60
attcagcaat aatgggcgtc tntcccaagg atccatatga cctcccaaag aacagtcaca    120
tcccttgtca ttatgacctg ctgccagtcc gagacagttc atcctcccct aagcaagagg    180
acagtggagg tagcagcagc aacagcagca gcagcagtga atgacaccaa aggaccgctt    240
ggtagccact ggaacccttt ccagaactgc tgtttggttc ttctccatcc tcaattttgc    300
cactttcatg tgaatgttag tcaattcggt gggcaatttt tggacatgaa ccagaaagct    360
gaaagctgag gctgacacgg actgtaggtg cttttttgttc aggtggattc gaaggagtta    420
gagatgtgat ttgccattgc tgttagtttt agaactatac ccgtgaagca tgacttattg    480
```

```
taagatgttg gctgaaagca tgaacttgca gaactccctc ggagacgcag gttgcagtgg      540
acattgggat tgttgcttga aaaattaaaa tttgaatatt ttctctctca tttgcatcat      600
agagctctac ctaggattgt acagtttacc ataaaattta cttcatgaaa gtgggaatca      660
ctgaacatgt agaagacaag gaacatattg ttaactcctg attcttaact ttattcaact      720

7ggactcagaa ttgtagggat aatatgaatg caggaggaaa cattctgtca ggcggtatga      780
ctggacagac tttgaatata ctctaaaagt ggacagaaaa tttacgaaaa tcttagattt      840
tgtttagaat gagaaaatat acaattagaa ttattttaga aatagtagga agtattgcag      900
aagtcaatac acaaatgtgc caggcagagg tggttttctc tgtttgactc tcaaccaact      960
tcagatctat gacattattc tgatcactgg ctccatcata catattcacc acttgagatt     1020
cataacatat caatagttat ttcataaata tagaaatgaa ataatttat ttttgacaga     1080 ctggatggaa tgagtgtgta atgattgata aaggttgtaa attttaaatg caagatgacg     1140
cttacgttct gtaaaccatt agtaatacat gctgtaatat agaattagtg gaacattttg     1200
attaatcttt ccctagaagt gactgaaata tttttgtgca tatttgagaa agggaacttt     1260
ccttttatta attgtcaatt tagagaaact atgcttaagc tggtcttttg cattgctaat     1320
gtgacatgta cccaactttt cattaatttg tatttccatt tttaaattgc atattctatg     1380
ttttgtagtg tttggattgt taatgaaaaa atattatatg ttcgttattc cttgtattat     1440
tgccacttat cttttgcttg ataaaaatgc gttgttcttt tttcttttgg agggacaaga     1500
tgaaaatata taatttgaat tgattaaaat tggtcgttac taaaatagta tagtaaaaaa     1560
aaaaaaaaag ggcggccg                                                   1578
```

<210> SEQ ID NO 11
<211> LENGTH: 843
<212> TYPE: DNA
<213> ORGANISM: Homo sapiens

<400> SEQUENCE: 11

```
gcctttagg gcagagattc ctgagctgcg ttttagggta cagattccct gtttgaggag       60
cttggcccct ctgtaagcat ctgactcatc tcagagatat caattcttaa acactgtgac     120
aacaggatct aaaatggctg acacatttgt ccttgtgtca cgttccatta ttttatttaa     180
aaacgtcagt aatcgtttta gcttcttttcc agcaaactct tctccacagt agcccagtcg     240
tggtaggata aattacggat atagtcattc taggggtttc agtcttttcg atctcaaggc     300
attgtgtgtt ttgttccggg actggtttgg ctgggacaaa gttagaactg cctgaagttc     360
gcacattcag attgttgtgt ccatggagtt ttaggagggg atggcctttc cggtcttcgg     420
acttccatcc tctcccactt ccatctggcg tcccacacct tgtccctgc acttctggat      480 gacacagggt gctgctgcct cctagtcttt gcctttgctg ggccttctgt gcaggagact     540
tggtctcaaa gctcagagag agccagtccg gtcccagctc ctttgtccct tcctcagagg     600
ccttccttga agatgcatct agactaccag ccttatcagt gtttaagctt attcctttaa     660
cataagcttc ctgacaacat gaaattgttg gggttttttg gcgttggttg atttgtttag     720
gttttgcttt atacccgggc caaatagcac ataacacctg gttatatatg aaatactcat     780
atgtttatga ccaaaataaa tatgaaacct catattaaaa aaaaaaaaa aaagggcgg       840 ccg                                                                   843
```

<210> SEQ ID NO 12
<211> LENGTH: 234

```
<212> TYPE: PRT
<213> ORGANISM: Homo sapiens

<400> SEQUENCE: 12

Ala Ala Ala Thr Pro Ser Lys Val Trp Gly Ser Ser Ala Gly Arg Ile
  1               5                  10                  15

Glu Pro Arg Gly Gly Arg Gly Ala Leu Pro Thr Ser Met Gly Gln
             20                  25                  30

His Gly Pro Ser Ala Arg Ala Arg Ala Gly Arg Ala Pro Gly Pro Arg
             35                  40                  45

Pro Ala Arg Glu Ala Ser Pro Arg Leu Arg Val His Lys Thr Phe Lys
 50                  55                  60

Phe Val Val Val Gly Val Leu Leu Gln Val Pro Ser Ser Ala Ala
 65                  70                  75                  80

Thr Ile Lys Leu His Asp Gln Ser Ile Gly Thr Gln Gln Trp Glu His
                 85                  90                  95

Ser Pro Leu Gly Glu Leu Cys Pro Pro Gly Ser His Arg Ser Glu Arg
                100                 105                 110

Pro Gly Ala Cys Asn Arg Cys Thr Glu Gly Val Gly Tyr Thr Asn Ala
            115                 120                 125

Ser Asn Asn Leu Phe Ala Cys Leu Pro Cys Thr Ala Cys Lys Ser Asp
130                 135                 140

Glu Glu Glu Arg Ser Pro Cys Thr Thr Thr Arg Asn Thr Ala Cys Gln
145                 150                 155                 160

Cys Lys Pro Gly Thr Phe Arg Asn Asp Asn Ser Ala Glu Met Cys Arg
                165                 170                 175

Lys Cys Ser Thr Gly Cys Pro Arg Gly Met Val Lys Val Lys Asp Cys
                180                 185                 190

Thr Pro Trp Ser Asp Ile Glu Cys Val His Lys Glu Ser Gly Asn Gly
            195                 200                 205

His Asn Ile Trp Val Ile Leu Val Val Thr Leu Val Val Pro Leu Leu
        210                 215                 220

Leu Val Ala Val Leu Ile Val Cys Cys Cys
225                 230

<210> SEQ ID NO 13
<211> LENGTH: 608
<212> TYPE: PRT
<213> ORGANISM: Mus musculus

<400> SEQUENCE: 13

Thr Arg Pro Ile Leu Val Ile His Asp Glu Gln Lys Gly Pro Glu Val
  1               5                  10                  15

Thr Ser Asn Ala Ala Leu Thr Leu Arg Asn Phe Cys Asn Trp Gln Lys
             20                  25                  30

Gln His Asn Pro Pro Ser Asp Arg Asp Ala Glu His Tyr Asp Thr Ala
             35                  40                  45

Ile Leu Phe Thr Arg Gln Asp Leu Cys Gly Ser Gln Thr Cys Asp Thr
 50                  55                  60

Leu Gly Met Ala Asp Val Gly Thr Val Cys Asp Pro Ser Arg Ser Cys
 65                  70                  75                  80

Ser Val Ile Glu Asp Asp Gly Leu Gln Ala Ala Phe Thr Thr Ala His
                 85                  90                  95

Glu Leu Gly His Val Phe Asn Met Pro His Asp Asp Ala Lys Gln Cys
                100                 105                 110
```

-continued

```
Ala Ser Leu Asn Gly Val Asn Gln Asp Ser His Met Met Ala Ser Met
        115                 120                 125

Leu Ser Asn Leu Asp His Ser Gln Pro Trp Ser Pro Cys Ser Ala Tyr
130                 135                 140

Met Ile Thr Ser Phe Leu Asp Asn Gly His Gly Glu Cys Leu Met Asp
145                 150                 155                 160

Lys Pro Gln Asn Pro Ile Gln Leu Pro Gly Asp Leu Pro Gly Thr Ser
                165                 170                 175

Tyr Asp Ala Asn Arg Gln Cys Gln Phe Thr Phe Gly Glu Asp Ser Lys
            180                 185                 190

His Cys Pro Asp Ala Ala Ser Thr Cys Ser Thr Leu Trp Cys Thr Gly
        195                 200                 205

Thr Ser Gly Gly Val Leu Val Cys Gln Thr Lys His Phe Pro Trp Ala
    210                 215                 220

Asp Gly Thr Ser Cys Gly Glu Gly Lys Trp Cys Ile Asn Gly Lys Cys
225                 230                 235                 240

Val Asn Lys Thr Asp Arg Lys His Phe Asp Thr Pro Phe His Gly Ser
                245                 250                 255

Trp Gly Met Trp Gly Pro Trp Gly Asp Cys Ser Arg Thr Cys Gly Gly
            260                 265                 270

Gly Val Gln Tyr Thr Met Arg Glu Cys Asp Asn Pro Val Pro Lys Asn
        275                 280                 285

Gly Gly Lys Tyr Cys Glu Gly Lys Arg Val Arg Tyr Arg Ser Cys Asn
    290                 295                 300

Leu Glu Asp Cys Pro Asp Asn Asn Gly Lys Thr Phe Arg Glu Glu Gln
305                 310                 315                 320

Cys Glu Ala His Asn Glu Phe Ser Lys Ala Ser Phe Gly Ser Gly Pro
                325                 330                 335

Ala Val Glu Trp Ile Pro Lys Tyr Ala Gly Val Ser Pro Lys Asp Arg
            340                 345                 350

Cys Lys Leu Ile Cys Gln Ala Lys Gly Ile Gly Tyr Phe Phe Val Leu
        355                 360                 365

Gln Pro Lys Val Val Asp Gly Thr Pro Cys Ser Pro Asp Ser Thr Ser
    370                 375                 380

Val Cys Val Gln Gly Gln Cys Val Lys Ala Gly Cys Asp Arg Ile Ile
385                 390                 395                 400

Asp Ser Lys Lys Lys Phe Asp Lys Cys Gly Val Cys Gly Gly Asn Gly
                405                 410                 415

Ser Thr Cys Lys Lys Ile Ser Gly Ser Val Thr Ser Ala Lys Pro Gly
            420                 425                 430

Tyr His Asp Ile Ile Thr Ile Pro Ile Gly Ala Thr Asn Ile Glu Val
        435                 440                 445

Lys Gln Arg Asn Gln Arg Gly Ser Arg Asn Asn Gly Ser Phe Leu Ala
    450                 455                 460

Ile Lys Ala Ala Asp Gly Thr Tyr Ile Leu Asn Gly Asp Tyr Thr Leu
465                 470                 475                 480

Ser Thr Leu Glu Gln Asp Ile Met Tyr Lys Gly Val Val Leu Arg Tyr
                485                 490                 495

Ser Gly Ser Ser Ala Ala Leu Glu Arg Ile Arg Ser Phe Ser Pro Leu
            500                 505                 510

Lys Glu Pro Leu Thr Ile Gln Val Leu Thr Val Gly Asn Ala Leu Arg
        515                 520                 525
```

```
Pro Lys Ile Lys Tyr Thr Tyr Phe Val Lys Lys Lys Glu Ser Phe
    530                 535                 540

Asn Ala Ile Pro Thr Phe Ser Ala Trp Val Ile Glu Glu Trp Gly Glu
545                 550                 555                 560

Cys Ser Lys Thr Cys Gly Lys Gly Tyr Lys Lys Arg Ser Leu Lys Cys
                565                 570                 575

Leu Ser His Asp Gly Gly Val Leu Ser His Glu Ser Cys Asp Pro Leu
            580                 585                 590

Lys Lys Pro Lys His Phe Ile Asp Phe Cys Thr Met Ala Glu Cys Ser
            595                 600                 605

<210> SEQ ID NO 14
<211> LENGTH: 218
<212> TYPE: PRT
<213> ORGANISM: Rattus rattus

<400> SEQUENCE: 14

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Tyr Asp Lys Lys Asn Tyr Val
    210                 215

<210> SEQ ID NO 15
<211> LENGTH: 247
<212> TYPE: PRT
<213> ORGANISM: Homo sapiens

<400> SEQUENCE: 15

Met Ser Met Ser Leu Glu Ile Thr Gly Thr Ser Leu Ala Val Leu Gly
1               5                   10                  15

Trp Leu Cys Thr Ile Val Cys Cys Ala Leu Pro Met Trp Arg Val Ser
            20                  25                  30
```

```
Ala Phe Ile Gly Ser Ser Ile Ile Thr Ala Gln Ile Thr Trp Glu Gly
         35                  40                  45

Leu Trp Met Asn Cys Val Gln Ser Thr Gly Gln Met Gln Cys Lys Met
     50                  55                  60

Tyr Asp Ser Leu Leu Ala Leu Pro Gln Asp Leu Gln Ala Ala Arg Ala
 65                  70                  75                  80

Leu Ile Val Val Ser Ile Leu Leu Ala Ala Phe Gly Leu Leu Val Ala
                 85                  90                  95

Leu Val Gly Ala Gln Cys Thr Asn Cys Val Gln Asp Glu Thr Ala Lys
             100                 105                 110

Ala Lys Ile Thr Ile Val Ala Gly Val Leu Phe Leu Leu Ala Ala Val
         115                 120                 125

Leu Thr Leu Val Pro Val Ser Trp Ser Ala Asn Thr Ile Ile Arg Asp
     130                 135                 140

Phe Tyr Asn Pro Leu Val Pro Glu Ala Gln Lys Arg Glu Met Gly Thr
145                 150                 155                 160

Gly Leu Tyr Val Gly Trp Ala Ala Ala Leu Gln Leu Leu Gly Gly
                165                 170                 175

Ala Leu Leu Cys Cys Ser Cys Pro Pro Arg Glu Lys Tyr Ala Pro Thr
             180                 185                 190

Lys Ile Leu Tyr Ser Ala Pro Arg Ser Thr Gly Pro Gly Thr Gly Thr
         195                 200                 205

Gly Thr Ala Tyr Asp Arg Lys Thr Thr Ser Glu Arg Pro Gly Ala Arg
     210                 215                 220

Thr Pro His His His Tyr Gln Pro Ser Met Tyr Pro Thr Arg Pro
225                 230                 235                 240

Ala Cys Ser Leu Ala Ser Glu
             245
```

<210> SEQ ID NO 16
<211> LENGTH: 551
<212> TYPE: PRT
<213> ORGANISM: Rattus rattus

<400> SEQUENCE: 16

```
Cys Ala Ser Leu Asn Gly Val Ser Gly Asp Ser His Leu Met Ala Ser
  1               5                  10                  15

Met Leu Ser Ser Leu Asp His Ser Gln Pro Trp Ser Pro Cys Ser Ala
             20                  25                  30

Tyr Met Val Thr Ser Phe Leu Asp Asn Gly His Gly Glu Cys Leu Met
         35                  40                  45

Asp Lys Pro Gln Asn Pro Ile Lys Leu Pro Ser Asp Leu Pro Gly Thr
     50                  55                  60

Leu Tyr Asp Ala Asn Arg Gln Cys Gln Phe Thr Phe Gly Glu Glu Ser
 65                  70                  75                  80

Lys His Cys Pro Asp Ala Ala Ser Thr Cys Thr Thr Leu Trp Cys Thr
                 85                  90                  95

Gly Thr Ser Gly Gly Leu Leu Val Cys Gln Thr Lys His Phe Pro Trp
             100                 105                 110

Ala Asp Gly Thr Ser Cys Gly Glu Gly Lys Trp Cys Val Ser Gly Lys
         115                 120                 125

Cys Val Asn Lys Thr Asp Met Lys His Phe Ala Thr Pro Val His Gly
     130                 135                 140

Ser Trp Gly Pro Trp Gly Pro Trp Gly Asp Cys Ser Arg Thr Cys Gly
145                 150                 155                 160
```

-continued

```
Gly Gly Val Gln Tyr Thr Met Arg Glu Cys Asp Asn Pro Val Pro Lys
            165                 170                 175

Asn Gly Gly Lys Tyr Cys Glu Gly Lys Arg Val Arg Tyr Arg Ser Cys
            180                 185                 190

Asn Ile Glu Asp Cys Pro Asp Asn Asn Gly Lys Thr Phe Arg Glu Glu
            195                 200                 205

Gln Cys Glu Ala His Asn Glu Phe Ser Lys Ala Ser Phe Gly Asn Glu
    210                 215                 220

Pro Thr Val Glu Trp Thr Pro Lys Tyr Ala Gly Val Ser Pro Lys Asp
225                 230                 235                 240

Arg Cys Lys Leu Thr Cys Glu Ala Lys Gly Ile Gly Tyr Phe Phe Val
                245                 250                 255

Leu Gln Pro Lys Val Val Asp Gly Thr Pro Cys Ser Pro Asp Ser Thr
            260                 265                 270

Ser Val Cys Val Gln Gly Gln Cys Val Lys Ala Gly Cys Asp Arg Ile
            275                 280                 285

Ile Asp Ser Lys Lys Phe Asp Lys Cys Gly Val Cys Gly Gly Asn
    290                 295                 300

Gly Ser Thr Cys Lys Lys Met Ser Gly Ile Val Thr Ser Thr Arg Pro
305                 310                 315                 320

Gly Tyr His Asp Ile Val Thr Ile Pro Ala Gly Ala Thr Asn Ile Glu
                325                 330                 335

Val Lys His Arg Asn Gln Arg Gly Ser Arg Asn Asn Gly Ser Phe Leu
                340                 345                 350

Ala Ile Arg Ala Ala Asp Gly Thr Tyr Ile Leu Asn Gly Asn Phe Thr
            355                 360                 365

Leu Ser Thr Leu Glu Gln Asp Leu Thr Tyr Lys Gly Thr Val Leu Arg
    370                 375                 380

Tyr Ser Gly Ser Ser Ala Ala Leu Glu Arg Ile Arg Ser Phe Ser Pro
385                 390                 395                 400

Leu Lys Glu Pro Leu Thr Ile Gln Val Leu Met Val Gly His Ala Leu
                405                 410                 415

Arg Pro Lys Ile Lys Phe Thr Tyr Phe Met Lys Lys Thr Glu Ser
                420                 425                 430

Phe Asn Ala Ile Pro Thr Phe Ser Glu Trp Val Ile Glu Glu Trp Gly
            435                 440                 445

Glu Cys Ser Lys Thr Cys Gly Ser Gly Trp Gln Arg Arg Val Val Gln
    450                 455                 460

Cys Arg Asp Ile Asn Gly His Pro Ala Ser Glu Cys Ala Lys Glu Val
465                 470                 475                 480

Lys Pro Ala Ser Thr Arg Pro Cys Ala Asp Leu Pro Cys Pro His Trp
                485                 490                 495

Gln Val Gly Asp Trp Ser Pro Cys Ser Lys Thr Cys Gly Lys Gly Tyr
            500                 505                 510

Lys Lys Arg Thr Leu Lys Cys Val Ser His Asp Gly Gly Val Leu Ser
            515                 520                 525

Asn Glu Ser Cys Asp Pro Leu Lys Lys Pro Lys His Tyr Ile Asp Phe
    530                 535                 540

Cys Thr Leu Thr Gln Cys Ser
545                 550
```